US011150126B2

(12) United States Patent
Wallace et al.

(10) Patent No.: US 11,150,126 B2
(45) Date of Patent: *Oct. 19, 2021

(54) SYSTEM AND METHOD FOR MAINTAINING RECIPE RATIOS WHEN MEASURING INGREDIENTS FOR CULINARY COMBINATIONS

(71) Applicant: Perfect Company, Inc., Vancouver, WA (US)

(72) Inventors: Michael Wallace, Vancouver, WA (US); Philip T. Odom, Portland, OR (US); Brian Richardson, Portland, OR (US); Darin Barri, Rolling Hills Estates, CA (US)

(73) Assignee: PERFECT COMPANY, INC., Vancouver, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/679,788

(22) Filed: Nov. 11, 2019

(65) Prior Publication Data
US 2020/0072658 A1 Mar. 5, 2020

Related U.S. Application Data

(63) Continuation of application No. 14/831,873, filed on Aug. 21, 2015, now Pat. No. 10,473,516, which is a
(Continued)

(51) Int. Cl.
*G01G 19/40* (2006.01)
*G01G 17/00* (2006.01)
(Continued)

(52) U.S. Cl.
CPC ............. *G01G 19/40* (2013.01); *A23L 35/00* (2016.08); *G01G 17/00* (2013.01); *G01G 19/00* (2013.01);
(Continued)

(58) Field of Classification Search
CPC ........ G01G 19/40; G01G 17/00; G01G 19/00; G01G 19/22; G01G 19/4144; G01G 19/56;
(Continued)

(56) References Cited

U.S. PATENT DOCUMENTS

| 6,837,148 B1 * | 1/2005 | Deschenes | A47J 27/00 99/325 |
| 2013/0101709 A1 * | 4/2013 | Rader | A23P 20/20 426/231 |

FOREIGN PATENT DOCUMENTS

GB 2251960 * 7/1992 ........... G01G 19/414

* cited by examiner

*Primary Examiner* — Randy W Gibson
(74) *Attorney, Agent, or Firm* — Rylander & Associates, PC; Philip R. M. Hunt

(57) ABSTRACT

A system and method for assisting a user in assembling a culinary combination according to a recipe. The system comprises a scale and a computing device configured to communicate with the scale. The system displays information regarding ingredients of the recipe and displays a progress of assembling the culinary combination based on the information from the scale. In some embodiments, a bar graph is displayed with a bar proportional to the measured amount of an ingredient of the recipe compared to a target amount for the ingredient. In some embodiments, the system displays a build column of one or more recipe blocks, representing actions or ingredients of the recipe. An active recipe block is displayed with a portion of the recipe block displayed in a different manner in proportion to the measured amount of an ingredient of the recipe compared to a target amount for the ingredient.

15 Claims, 18 Drawing Sheets

Related U.S. Application Data continuation of application No. 14/339,126, filed on Jul. 23, 2014, now Pat. No. 9,645,007, which is a continuation of application No. 13/918,984, filed on Jun. 16, 2013, now Pat. No. 8,829,365, which is a continuation of application No. 61/800,252, filed on Mar. 15, 2013.

(51) Int. Cl.

| | | |
|---|---|---|
| *G01G 19/22* | (2006.01) | |
| *G01G 19/414* | (2006.01) | |
| *G01N 33/02* | (2006.01) | |
| *G06F 13/38* | (2006.01) | |
| *A23L 35/00* | (2016.01) | |
| *G01G 19/00* | (2006.01) | |
| *G01G 19/56* | (2006.01) | |
| *G09B 5/02* | (2006.01) | |

(52) U.S. Cl.
CPC ......... *G01G 19/22* (2013.01); *G01G 19/4144* (2013.01); *G01G 19/56* (2013.01); *G01N 33/02* (2013.01); *G06F 13/382* (2013.01); *G09B 5/02* (2013.01); *A23V 2002/00* (2013.01)

(58) Field of Classification Search
CPC ....... A23L 35/00; G01N 33/02; G06F 13/382; A23V 2002/00
See application file for complete search history.

SYSTEM AND METHOD FOR MAINTAINING RECIPE RATIOS WHEN MEASURING INGREDIENTS FOR CULINARY COMBINATIONS

CROSS-REFERENCE TO RELATED APPLICATION

This application is a continuation of co-pending U.S. Non-Provisional application Ser. No. 14/831,873, filed 21 Aug. 2015, which is a continuation of U.S. Non-Provisional application Ser. No. 14/339,126, filed 23 Jul. 2014, which is a continuation of U.S. Non-Provisional application Ser. No. 13/918,984, filed 16 Jun. 2013, which in turn claims the benefit of, and priority to U.S. Provisional patent application Ser. No. 61/800,252 filed on 15 Mar. 2013, all incorporated herein by reference.

FIELD OF THE INVENTION

The present invention relates to weight scales. More particularly, the present invention relates to interactive systems of weight scales and computing devices.

BACKGROUND

Recipes are commonly used to create culinary combinations of food or drink. As used herein, culinary combinations will include creations of mixology and of cooking. The foundations of all recipes are culinary ratios. A culinary ratio is a fixed proportion of one or more ingredients of a recipe relative to another. These ratios are fundamental to the crafts of cooking and mixology. Understanding that recipes are ratios allow one to consistently scale or adjust recipes and to fix a recipe if one makes a mistake and adds too much of a certain ingredient.

When preparing food or drinks, it is best to use weight rather than volume for measuring most ingredients. Properties of a culinary combination are more closely dependent on the ratio of the weights or masses of ingredients, than on their volumes. For a culinary combination to have the desired properties, the ratios of the masses or weights of the ingredients must be achieved. Volumetric measurements may be convenient approximations for weight, but it the weight or mass of the ingredients that is desired. Measuring by volume can introduce inaccuracies. The volume of a certain mass of a material can change based on environmental conditions such as temperature, pressure and humidity. Because of this, powder ingredients like flour are in particular more accurately measured by weight than by volume. The volumetric measurement of liquids has other sources of inaccuracy. The shape of the target container, the viewing angle of the user, and the surface tension of the liquid can easily cause a 20% variation when visually judging what is "full" for small amounts of liquid. Weighing ingredients is the most reliable and consistent form of measuring, and it is the preferred method when it comes to using culinary ratios.

The standard digital scale can measure in metric or imperial units (also referred to as the U.S. customary units or avoirdupois units). A scale measuring a liquid detects weight, but some are configured to report the amount detected in volume units such as milliliters or fluid ounces (defined as $\frac{1}{16}$ of a pint or $\frac{1}{128}$ of a gallon in the US customary units system). However, this assumes the liquid is water or has a similar volume/weight ratio (density) as water. Some liquids have densities that are different from water, which can throw off the accuracy of using a scale to determine volume. For example, one milliliter is one gram of water and 30 grams of water is approximately 1 fluid ounce. The specific gravity of water is 1.00 (specific gravity is the ratio of density of fluid in question to the density of water). The specific gravity of simple syrup is typically 1.33. If a recipe calls for a 1 fluid ounce of simple syrup, weighing out one ounce of simple syrup will be rather inaccurate unless the scale knows the specific gravity of the fluid it is weighing and calculates fluid ounces accordingly.

Using a scale to maintain ratios can be especially challenging for standard cocktail recipes, which typically specify volume measurements. As an example a classic margarita recipe calls for the following ingredients:

| | |
|---|---|
| 60 ml tequila | (2 fluid oz.) |
| 30 ml Cointreau | (1 fluid oz.) |
| 23 ml fresh Lime Juice | (¾ fluid oz.) |

The specific gravity for each ingredient is approximately:

| | |
|---|---|
| Tequila | (0.95) |
| Cointreau | (1.04) |
| Lime Juice | (1.4) |

To measure a correct ratio by weight, the specific gravity of each ingredient must be considered. A scale assuming the specific gravity of water to measure ingredients would yield:
  60 grams tequila=68.01 ml=(2.3 fluid oz)
  30 grams Contreau=29.0 ml=(0.98 fluid oz)
  23 grams fresh lime juice=13.6 ml=(0.46 fluid oz)
This would result in significantly different ratios of ingredients than the original recipe and would not taste the same. A correct measurement incorporating the specific gravity of each ingredient would measure the following:
  57 grams Tequila=(2 fluid oz.)
  31.2 grams Cointreau=(1 fluid oz.)
  32.2 grams Lime Juice=(¾ fluid oz.)

The standard digital kitchen scale typically has a "tare" button. This is used to subtract the current weight on the smart scale 102, setting the current measured weight to zero. Using this button allows the weight of a containing vessel (like a bowl or glass) to be eliminated when measuring an ingredient. Using this button sequentially to build a multistep recipe allows each ingredient to be measured independently as it is added.

This is a useful system and minimizes the use of containers. However, it does not have any awareness of the ingredients being measured or specific actions of the recipe. What if you make a mistake reading a recipe? Let's say a recipe asks for 70 grams of grape juice and 100 grams of apple juice and the user puts them in backwards (70 grams of apple juice and 100 grams of grape juice). It can be difficult to fix this, especially in the context of the entire recipe, where the measured amount for each ingredient must now be precisely altered to maintain a proper ratio.

Another problem is scaling a recipe. Simple scaling is practicable in one's head when doubling (2×) or halving (½) the recipe. However, other scaling changes, like making 30% less, or 1.75 times more, become more complicated. The common digital kitchen scale offers no assistance here.

BRIEF DESCRIPTION OF THE DRAWINGS

The present invention will be described by way of exemplary embodiments, but not limitations, illustrated in the accompanying drawings in which like references denote similar elements, and in which.

The accompanying drawings, which are incorporated into and constitute a part of this specification, illustrate one or more embodiments of the invention and, together with the detailed description, serve to explain the principles and implementations of the invention.

DETAILED DESCRIPTION

Figure 1:
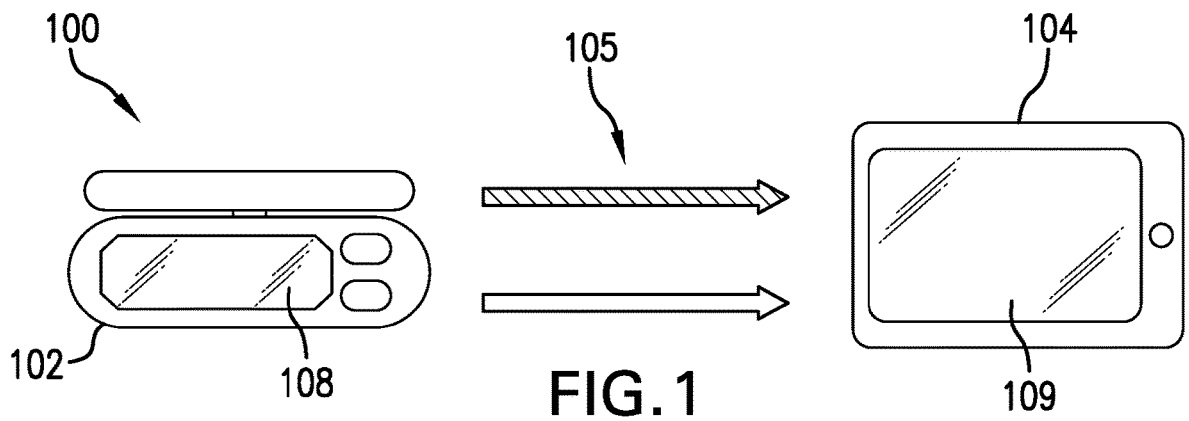
FIG. 1 shows an embodiment of the culinary ratio system with a one-way data connection from the smart scale to the smart device.

Before beginning a detailed description of the subject invention, mention of the following is in order. When appropriate, like reference materials and characters are used to designate identical, corresponding, or similar components in different figures. The figures associated with this disclosure typically are not drawn with dimensional accuracy to scale, i.e., such drawings have been drafted with a focus on clarity of viewing and understanding rather than dimensional accuracy.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application and business related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Use of directional terms such as "upper," "lower," "above," "below", "in front of," "behind," etc. are intended to describe the positions and/or orientations of various components of the invention relative to one another as shown in the various Figures and are not intended to impose limitations on any position and/or orientation of any embodiment of the invention relative to any reference point external to the reference.

The culinary ratio system 100 represents a significant advance in technology assisted cooking and mixology. As shown in the embodiments of FIGS. 1-6, the culinary ratio system 100 has a smart scale 102, a smart device 104 (computing device) and a communication connection 105 there between. Examples of the smart device 104 include a personal computer and mobile device such as a tablet computer or a mobile phone. The communication connection 105 can be wired or wireless and may be one-way or two-way. A smart scale 102 using a two-way link with a smart device 104 provides even more functionality.

The culinary ratio system 100 has a software app on the smart device 104 which is configured to receive real-time information from the smart scale 102. The app has access to information regarding actions, ingredients, and target amounts involved in a recipe. The app presents a user with actions to be performed and ingredients to be added.

The app is configured to assist the user in maintaining the culinary ratios of a recipe. The app is configured to accept input so that a user can change the overall serving size for the recipe at any time and the target amounts of each ingredient are automatically re-calculated and displayed. If too much of one ingredient is added, the app detects this and helps the user maintain the proper ratios. The number of servings is recalculated and displayed along with new target amounts for all other ingredients.

The culinary ratio system 100 has one or more graphical displays to show the real-time amount for any ingredient being added and may also show which ingredients have been added, which are left to be added, which actions have been performed, and which have still to be performed. In the preferred embodiment, there is a scale display 108 that is part of the smart scale 102 and a smart device display 109 that is part of the smart device 104. Both may be used for displaying information about recipe ingredients. Other embodiments may use only one of these displays.

In the preferred embodiment, the smart scale 102 has a button pad 110 (see FIG. 2) that can provide additional information for the app. Button presses can be sent to the app and used to invoke functions like: Change units; Next ingredient; Go back; Pause/Resume; and Adjust Ratio. The smart device 104 is also configured to provide a way for the user to provide information or enter commands to the app, such as a mouse, a keyboard or touch screen functionality in the smart device display 109.

The scale display 108 (see FIG. 4) can display real-time information for each ingredient including: a current ingredient indicator 132 showing the name of current ingredient;

a connection status indicator 134 showing the connection status with the smart device 104; a measurement progress indicator 136 (such as a bar graph) showing an amount of the current ingredient added proportional to its target amount; a target amount indicator 138 showing the target amount for the current ingredient; and a measured amount indicator 140 showing the measured amount of the current ingredient.

The smart scale 102 may have lights and audio that can be used to help inform the user when pouring/adding an ingredient. This may be easier for some users when pouring—it allows them to look at the smart scale 102 instead of a smart device display 109. For example, the color of an LED can slowly change from green to red as an ingredient is added and approaches its target amount. Audio prompts from the smart device can be played though the smart scale 102 to call out ingredients and progress. Timers can also be started for actions requiring timing. These timers can be displayed on either the smart device 104 or the smart scale 102. An optional microphone in the smart scale 102 or the smart device 104 can be used for voice prompts/commands like "Next", "Start Timer", etc.

One-Way Communications Connection

FIG. 1 shows an embodiment of the culinary ratio system 100 with a one-way data connection from the smart scale 102 to the smart device 104. This connection can be wired or wireless. Data transferred and functions enabled for this configuration include: Real-time scale data; Button events; and Container presence.

Real-Time Scale Data.

Since there is a way for the smart device 104 to receive real-time data from the smart scale 102 in this configuration, the app on the smart device 104 performs all the necessary tare operations and unit calculations. The scale display 108 may simply show a "connected" message or its own independent weight information.

Figure 2:
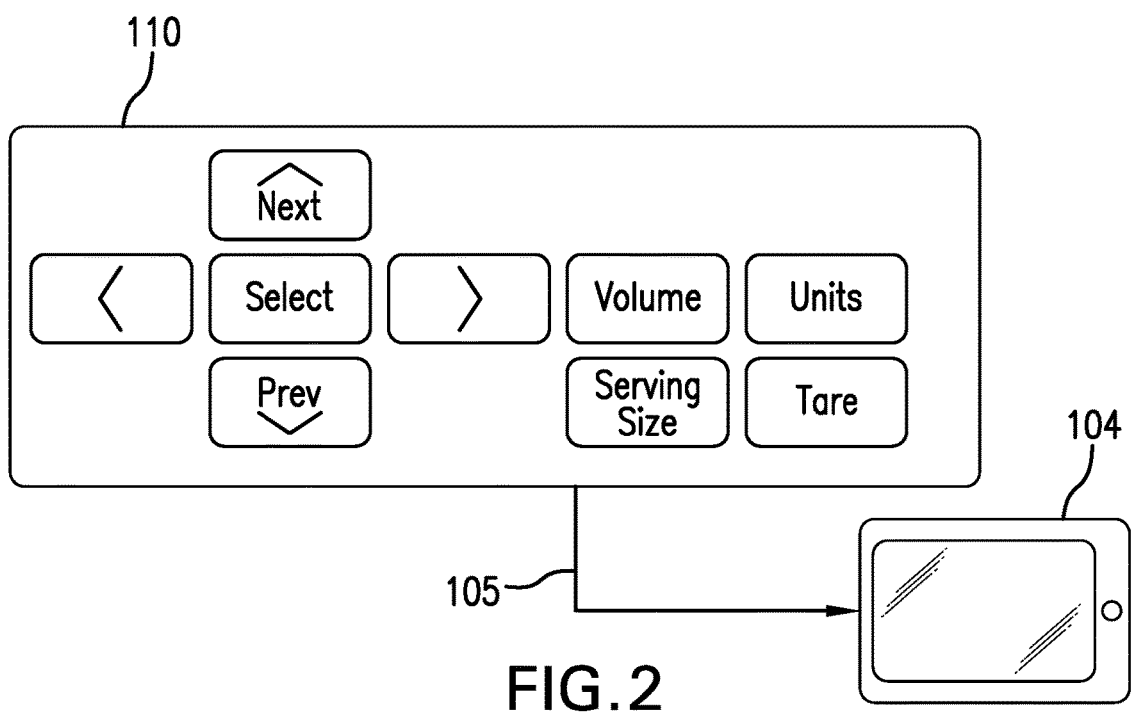
FIG. 2 shows a button pad on the smart scale.

Button Events (FIG. 2).

Button presses or capacitive sensor touches on button pad 110 of the smart scale 102 are detected and sent to the smart device 104 in real-time. Some possible button functions include: Unit Selection, Tare, Next, Back, Pause, Resume, and Serving Size.

Container Presence.

The presence of a container can be detected by the smart scale 102 either by weight or by means of a sensor and this information sent to the smart device 104.

Two-Way Communications Connection

Figure 3:
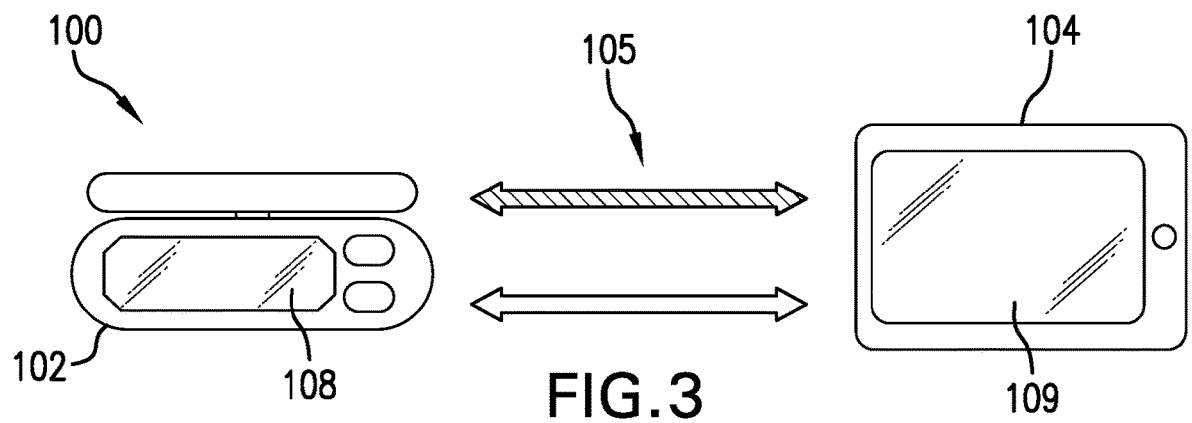
FIG. 3 shows an embodiment of the culinary ratio system with a two-way data connection from the smart scale to the smart device.

FIG. 3 shows an embodiment of a culinary ratio system 100 with a smart scale 102 using two-way communication with a smart device 104. This connection can be wired or wireless. A two-way communications connection has more options for synchronization and culinary workflow enhancement. Data transferred and functions enabled for this configuration include: Real-time scale data; Button events; Container presence; Scale display; Measurement/Unit Synchronization; Audio; LEDs; Buttons; and Microphone.

Figure 4:
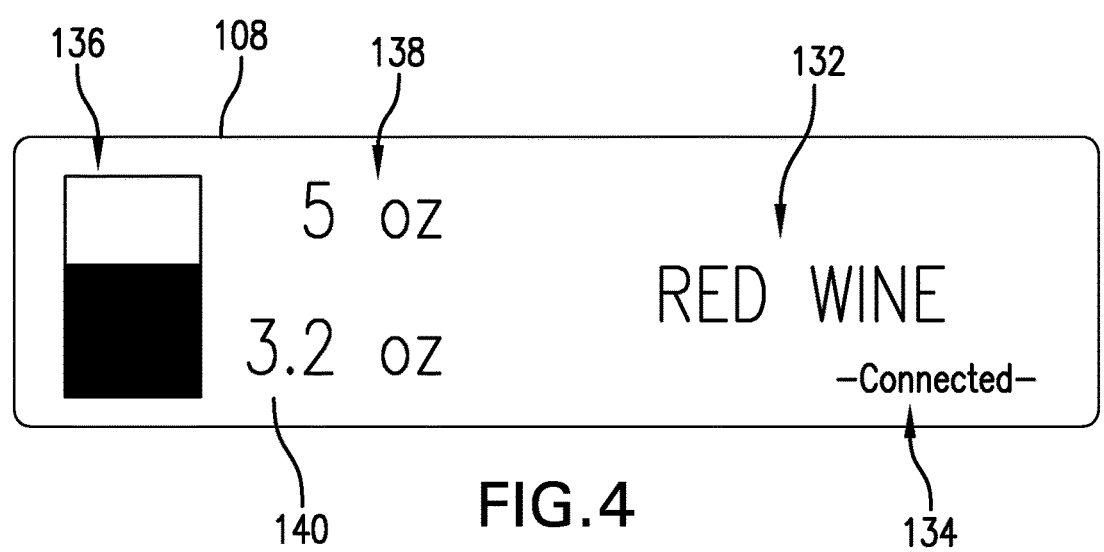
FIG. 4 shows a display on the smart scale.

Scale Display (FIG. 4).

In embodiments with a two-way communications connection, the scale display 108 can be synchronized and controlled by the app. Possible information displayed includes: Name of the current ingredient; Target amount of current ingredient; Amount/weight needed for the current ingredient (not shown in example); Real-time progress of measurement (graphical and/or numeric); Measured amount of current ingredient; Connection status with Smart Device; Measurement Units; and Serving Size/Scaling factor.

Measurement/Unit Synchronization.

Because the smart device 104 can send commands to the smart scale 102, either the smart scale 102 or the smart device 104 can perform actions like "tare". These actions can be synchronized with the recipe. Units and measurements can be synchronized in real-time.

Audio.

In some embodiments, the smart scale 102 has a speaker (not shown) for playing audio prompts and instructions. These commands may be generated by and played from the app. The audio connection between the smart scale 102 and the smart device 104 may be digital or analog.

LEDs.

In some embodiments, the smart scale 102 has LEDs (not shown). The LEDs on the smart scale 102 can be controlled by the app for real-time feedback. This control can be any combination of the following: Blinking/Pulsing; Brightness; Color; and individual LED controlled separately.

Container Presence.

The presence of a container can be detected by the smart scale 102 either sensing the weight of the container or by using a different type of sensor. Information of the presence of the container may be sent to the app on the smart device 104.

Buttons (FIG. 2).

Button presses or capacitive sensor touches on the button pad 110 can be detected and sent to the smart device 104 in real-time. These buttons can be used to control the app directly. Some possible button functions include: Unit Selection; Tare; Next; Back; Pause; Resume; Serving Size/Scale; Start/Stop Timer; and Adjust Ratio.

Microphone.

In some embodiments, the smart scale 102 has a microphone (not shown) that can record voice commands from the user and send them to the app for processing. A microphone/speaker combination on the smart scale 102 can be used to accomplish hands-free voice links with another remote user (like a phone call) during cooking. The audio connection for the microphone to the smart device 104 can be analog or digital. Voice commands could include: "Pause"; "Resume"; "Next"; "Back"; and "Start Timer".

Wired Connection Example: Audio Jack

Figure 5:
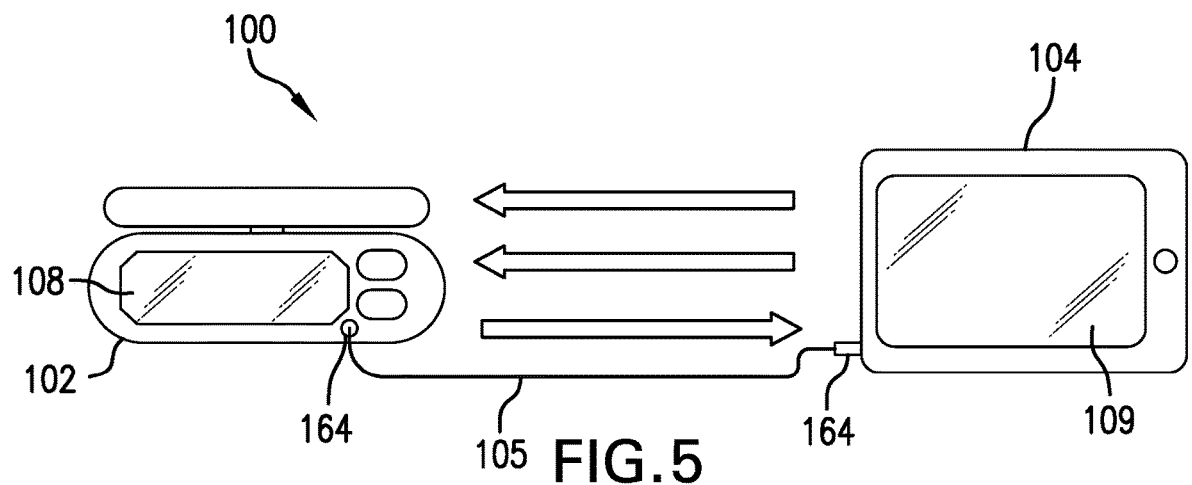
FIG. 5 shows an embodiment of the culinary ratio system 100 that uses an audio jack connection between the smart scale and smart device.

FIG. 5 shows an embodiment of the culinary ratio system 100 that uses an audio jack connection and associated communication protocols instead of USB or other standard or custom protocols. As smart devices become more popular it is increasingly difficult to support wired peripheral devices. This is due to the proliferation of different connectors on devices. The only standardized connector across the vast majority of devices is the headphone/microphone port, more commonly called an audio jack 164. This is a four-connector audio jack 164 that has: Ground; Microphone In; Left Audio Out; and Right Audio Out.

The smart scale 102 sends real-time data as analog audio data on the microphone channel, as illustrated in FIG. 5. Software in the app filters and decodes the data. An audio backchannel sends simple commands and data back to the smart scale 102 using one of the audio channels. The other audio channel can be used to play audio through a speaker in the smart scale 102.

Using the Culinary Ratio System

To aid the user in following a recipe and measuring multiple ingredients the culinary ratio system 100 presents an organized view of tasks. Major functions of the culinary ratio system 100 include:

Display ingredients and actions in a logical order for recipe assembly.

Display progress of recipe construction.

Display target containers and tools as needed in recipe construction.

Help the user to maintain proper ratios during construction, including how best to fix any errors.

Allow the user to easily scale and adjust the recipe.

Allow easy and accurate measurement units change/selection.

Allow for easy substitutions.

Figure 6:
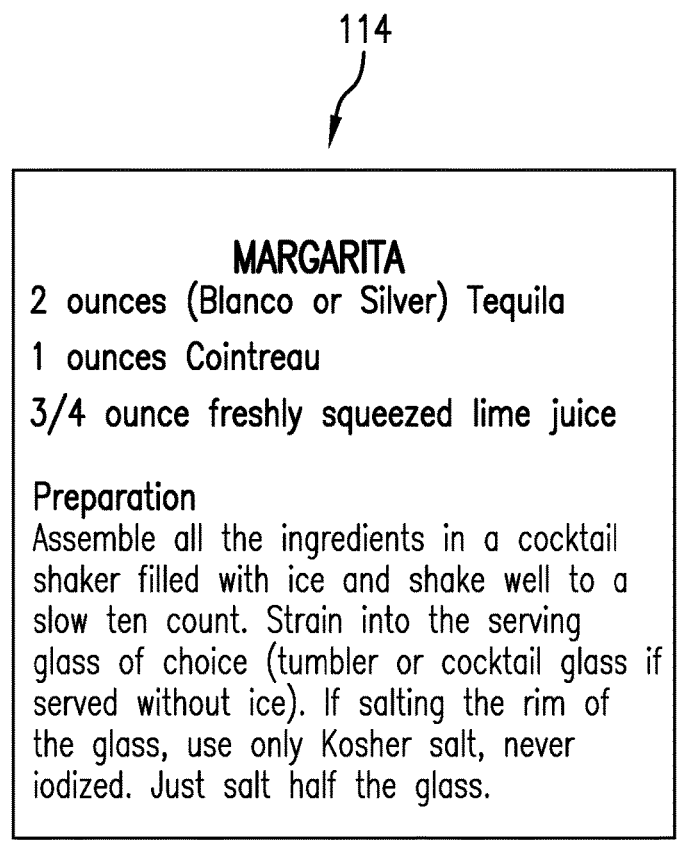
FIG. 6 shows a basic margarita recipe in traditional recipe form as it would typically be presented in a recipe book.
Figure 7:
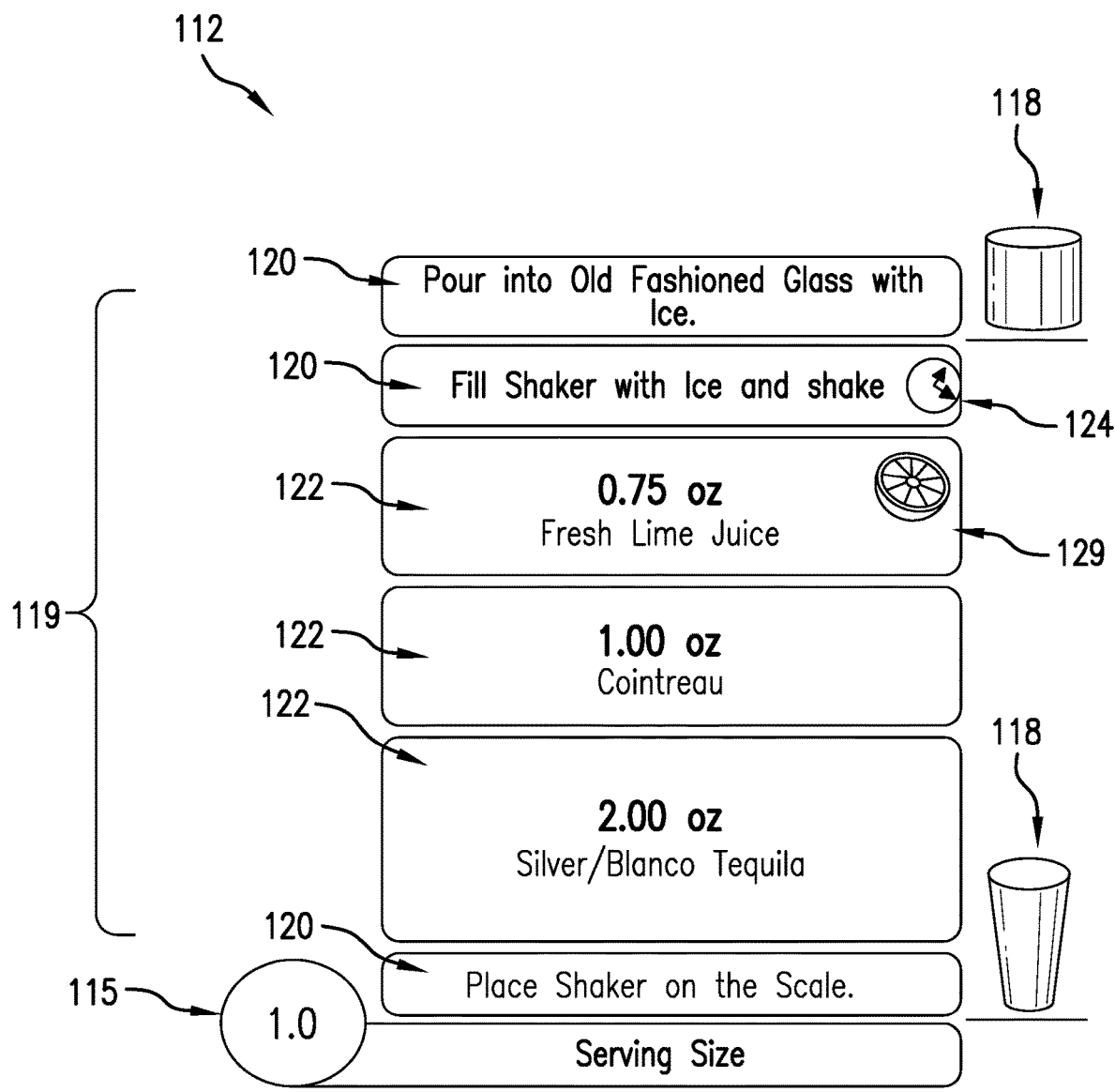
FIG. 7 shows the same basic margarita recipe displayed by the culinary ratio system in an interactive form called a build column.
Figure 22:
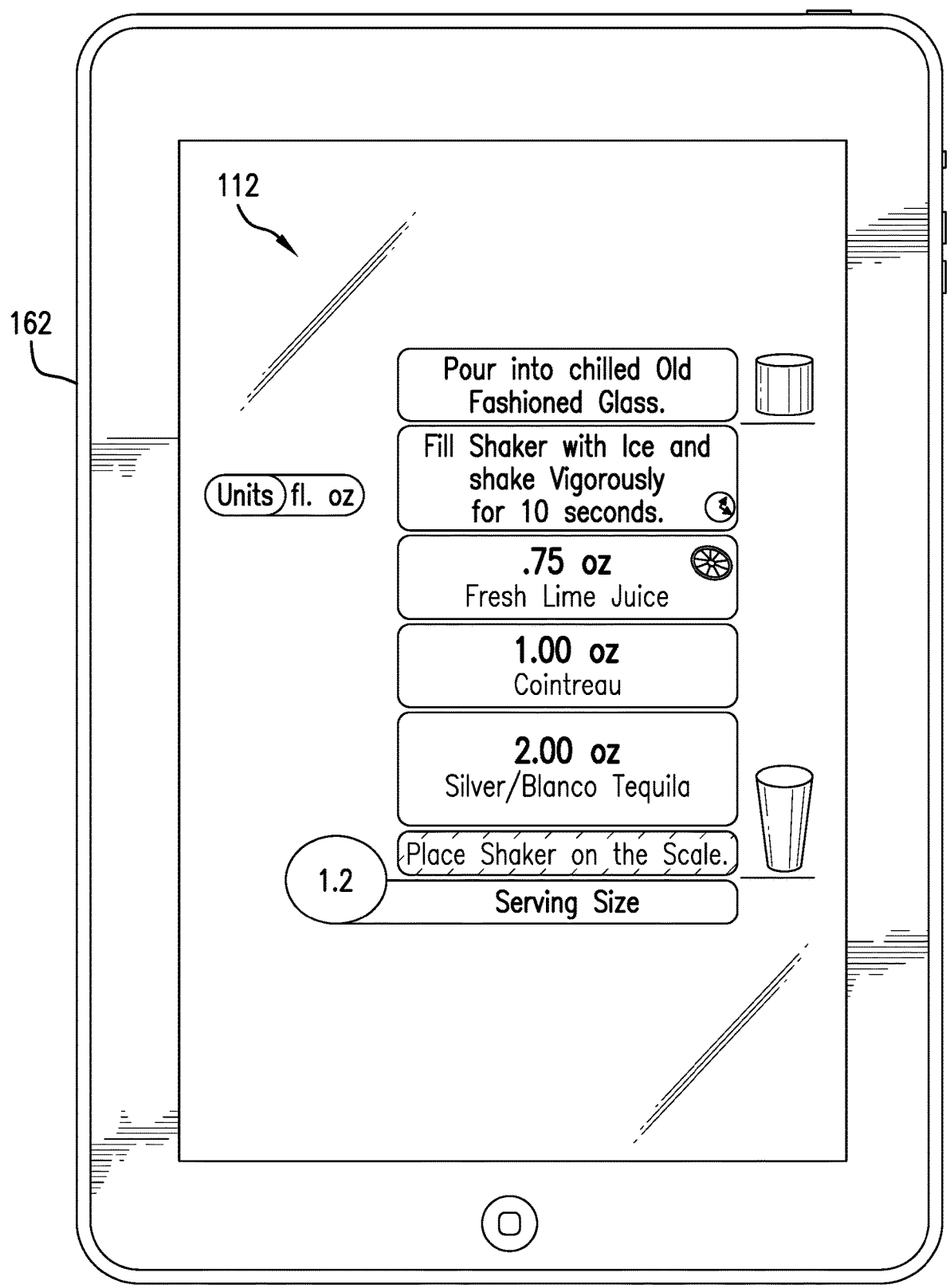
FIGS. 22 and 23 show the build column 112 displayed on a tablet computer.
Figure 23:
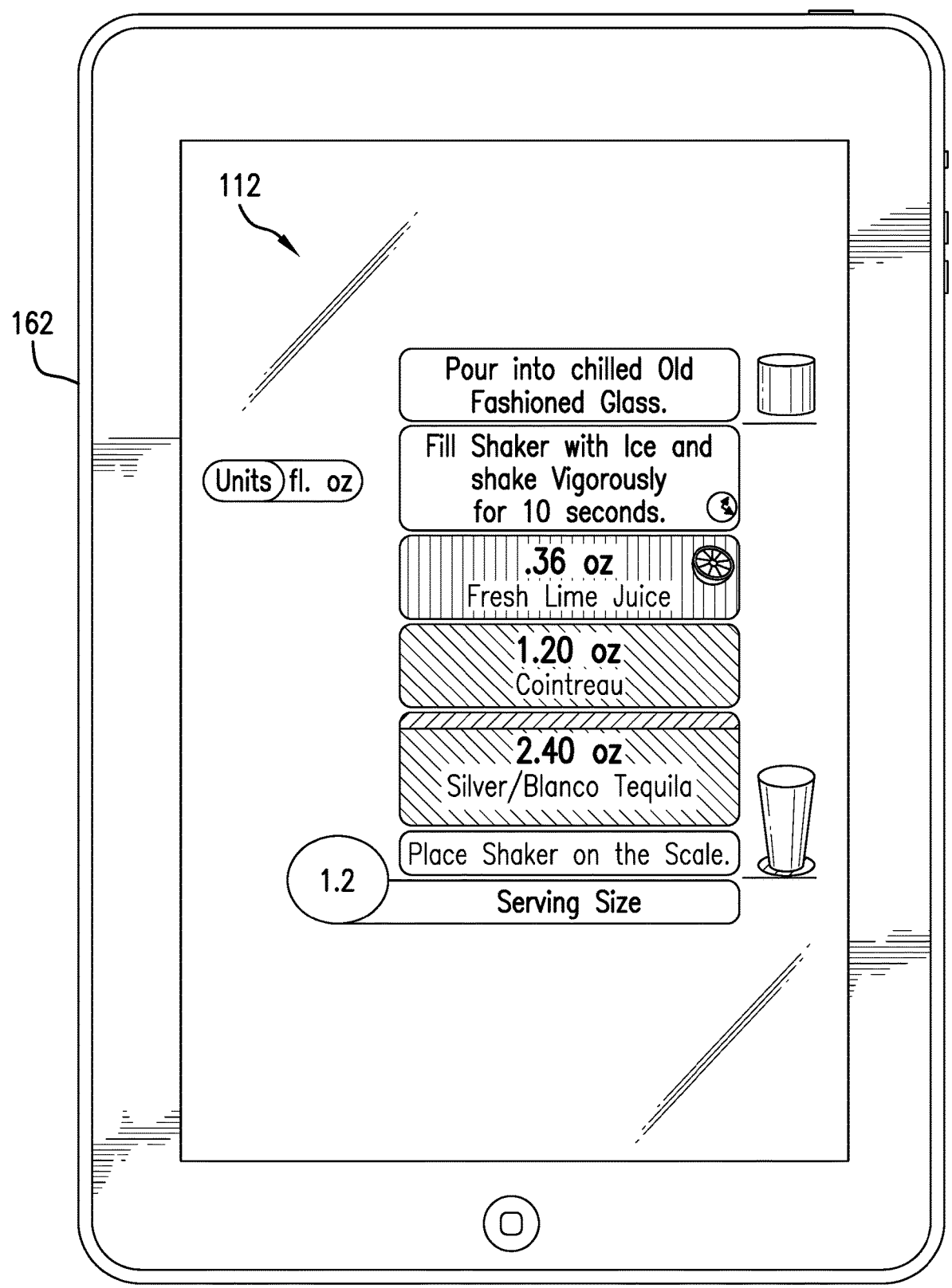

The culinary ratio system 100 displays ingredients and actions of a recipe in a logical and intuitive order. FIG. 6 shows a basic margarita recipe in traditional recipe form 114 as it would typically be presented in a recipe book. FIG. 7 shows the same basic margarita recipe displayed by the culinary ratio system 100 in an interactive form called a build column 112. The build column 112 clearly displays information such as serving size, actions, ingredients, containers, and recommended order of actions and ingredients to make the recipe. All of this information is easily seen with a simple visual scan of the build column 112. In the preferred embodiment, the build column 112 is displayed on the smart device display 109. For example, FIGS. 22 and 23 show the build column 112 displayed on a tablet computer 162. Other embodiments of the culinary ratio system 200 may display ingredients and actions of a recipe in formats other than the build column 112, using formats such as pie charts, wheels, inclines, ladders or the like.

FIG. 7 shows some of the build column 112 features. A serving size block 115 is displayed, typically at the bottom. A target serving size indicator 116 is displayed with the serving size block 115, displaying a target serving size of the recipe. The target serving size is initially the serving size called for by the recipe, but the culinary ratio system 100 allows the user to change target serving size. This target serving size can be in absolute units or relative units. When in absolute units, the target serving size is the amount per standard serving called for by the recipe. When in relative units, the target service size is a scaling factor, representing the number of standard servings. In some embodiments, the app allows the user to switch serving size mode between absolute and relative serving size units. In the preferred embodiment, the default is the relative serving size units.

The build column 112 has one or more recipe blocks 119, representing steps of the recipe. In the depicted embodiment, the build column 112 is shown as comprising recipe blocks 119 that are stacked vertically. However, in other embodiments, the recipe blocks 119 may be arranged in other ways, such as in a horizontal row or in montage. The recipe blocks may be of various types, including recipe action blocks 120 and recipe ingredient blocks 122. A recipe action block 120 is associated with an action step of the recipe. Information related to the associated action step is displayed with the recipe action block 120. Such information typically includes a text description of the action step. A recipe action block 120 can also include a timer icon 124 for an action that the recipe calls to be performed for a specific length of time, like baking, simmering, or mixing. The timer icon may be associated with a timer function of the app that can be set to play an audio alarm or send an email or text. The timer function may be invoked by the user or automatically by the app.

A recipe ingredient block 122 is associated with a step of adding one of the ingredients of the recipe. In some embodiments, each recipe ingredient block 122 has a size based on the target amount of the ingredient in the recipe. In some embodiments, each recipe ingredient block 122 has a small, medium, or large size based on the target amount of the ingredient relative to the other ingredients in the recipe. Optionally, the same size recipe block could be used for all ingredients and actions. As each recipe block becomes active, it could expand to a larger block with more information, and then shrink as the next recipe block is activated. An ingredient icon 129 can also be displayed with a recipe ingredient block 122 to indicate the ingredient's type like fruit juice, powder, or liquid, or to indicate a particular ingredient.

In the depicted embodiment, recipe construction is displayed from bottom to top. The first action in the build column 112 of FIG. 7 is setting a shaker on the smart scale 102. On the right, target container icons 118 for each build phase are placed in a chronological relationship with the build column 112.

Figure 8:
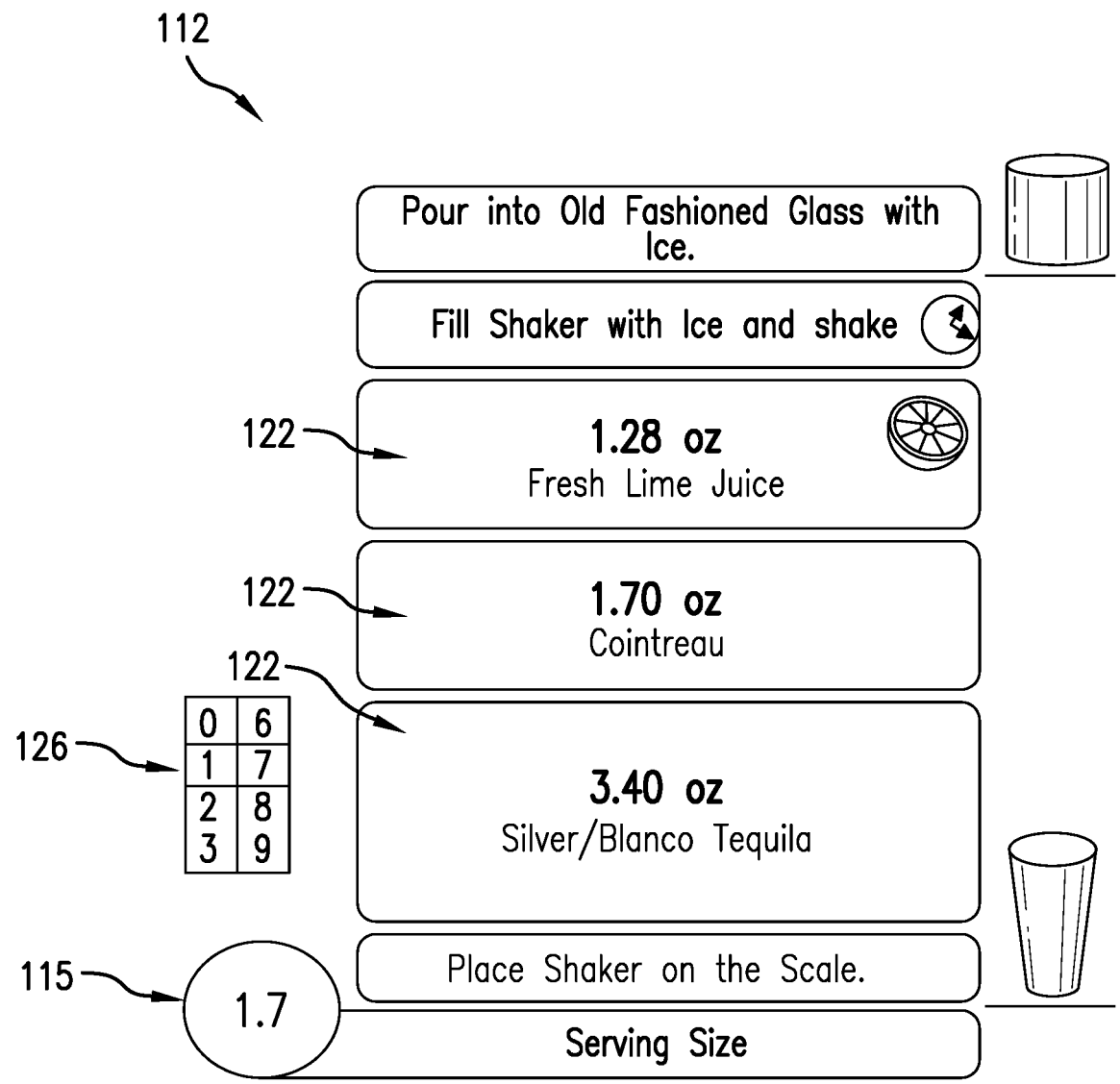
FIG. 8 shows how a recipe can be scaled with the culinary ratio system.

FIG. 8 shows how a recipe can be scaled with the culinary ratio system. If the user selects the serving size block 115, a serving size pop-up 126 appears, allowing the user to change/edit the target serving size of the recipe, changing either the amount or scaling factor, depending on which serving size mode the app is running. After a new serving size is selected, the target amounts of the ingredients of the recipe are changed in real-time showing the new target amounts. Changing the target serving size can also cause the target containers to be changed to larger, smaller, or more containers.

Another way to scale a recipe with the culinary ratio system 100 is to edit the amount used by one ingredient. The user selects one of the ingredients and then selects the target amount for the ingredient, which will cause the app to bring up an amount editor. The user simply enters a new target amount for this ingredient. The app changes the scaling factor of the recipe accordingly to maintain the culinary ratios. Then the target amounts for the other ingredients in rest of the build column 112 are automatically updated according to the scaling factor.

One more way to adjust the scale of a recipe with the culinary ratio system 100 is simply to add a larger amount for one of the ingredients during assembly of the recipe. The app may automatically change the scaling factor of the recipe if the measured amount of an ingredient exceeds the target amount for the ingredient, or in some embodiments, an upper threshold set slightly above the target amount. The app changes the scaling factor of the recipe accordingly to maintain the culinary ratios.

Figure 9:
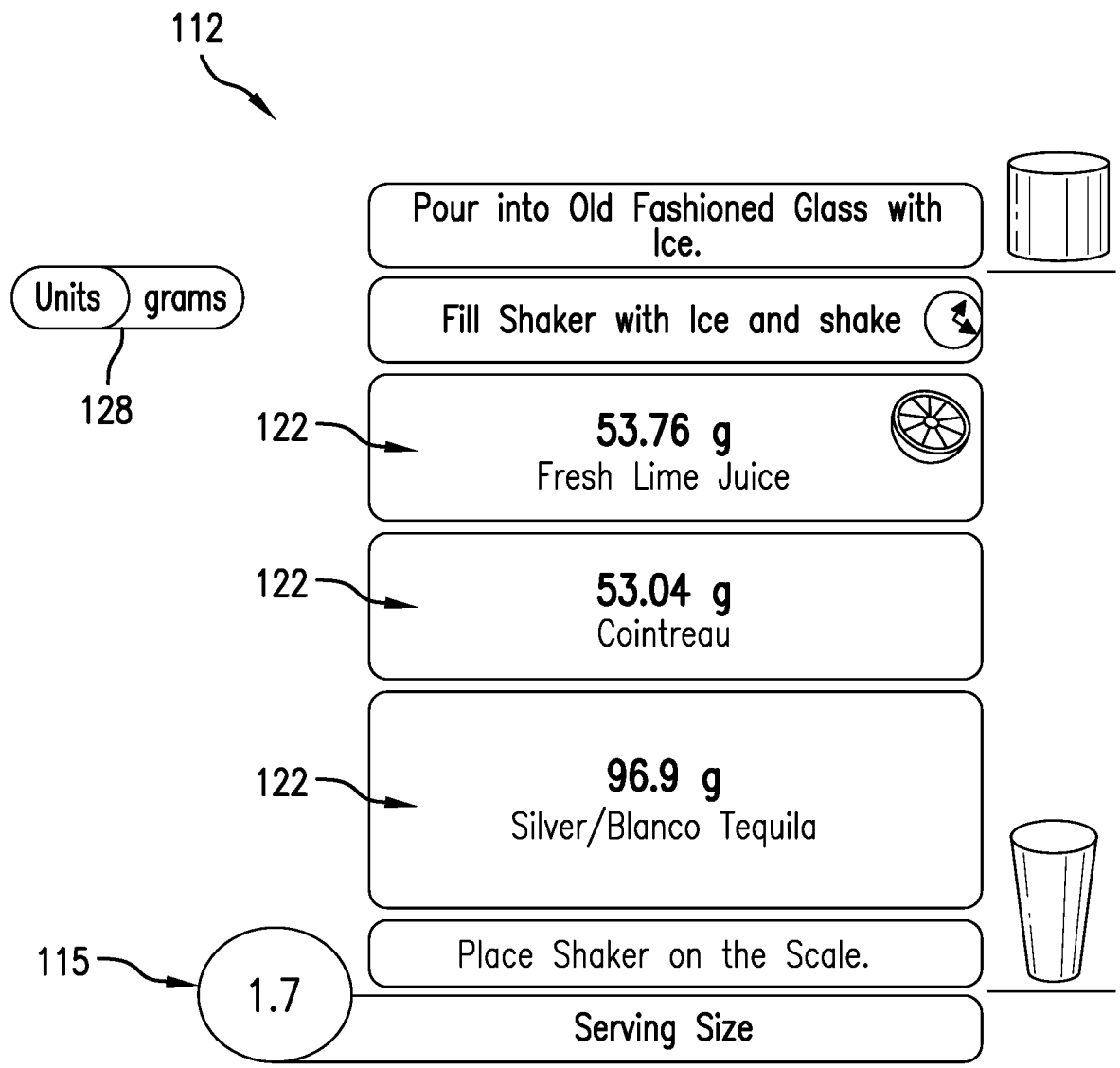
FIG. 9 shows how the build column changes when different measurement units are selected.

FIG. 9 shows how the build column 112 changes when different measurement units are selected. A measurement unit selection icon 128 is displayed with the build column 112. In this case, the measurement units have changed from a volume unit (fluid ounces) to a weight unit (grams). The build column immediately updates the target amounts for all ingredients to grams. For liquid ingredients, the app uses specific gravity constants for each ingredient to calculate accurate target amounts.

Figure 10:
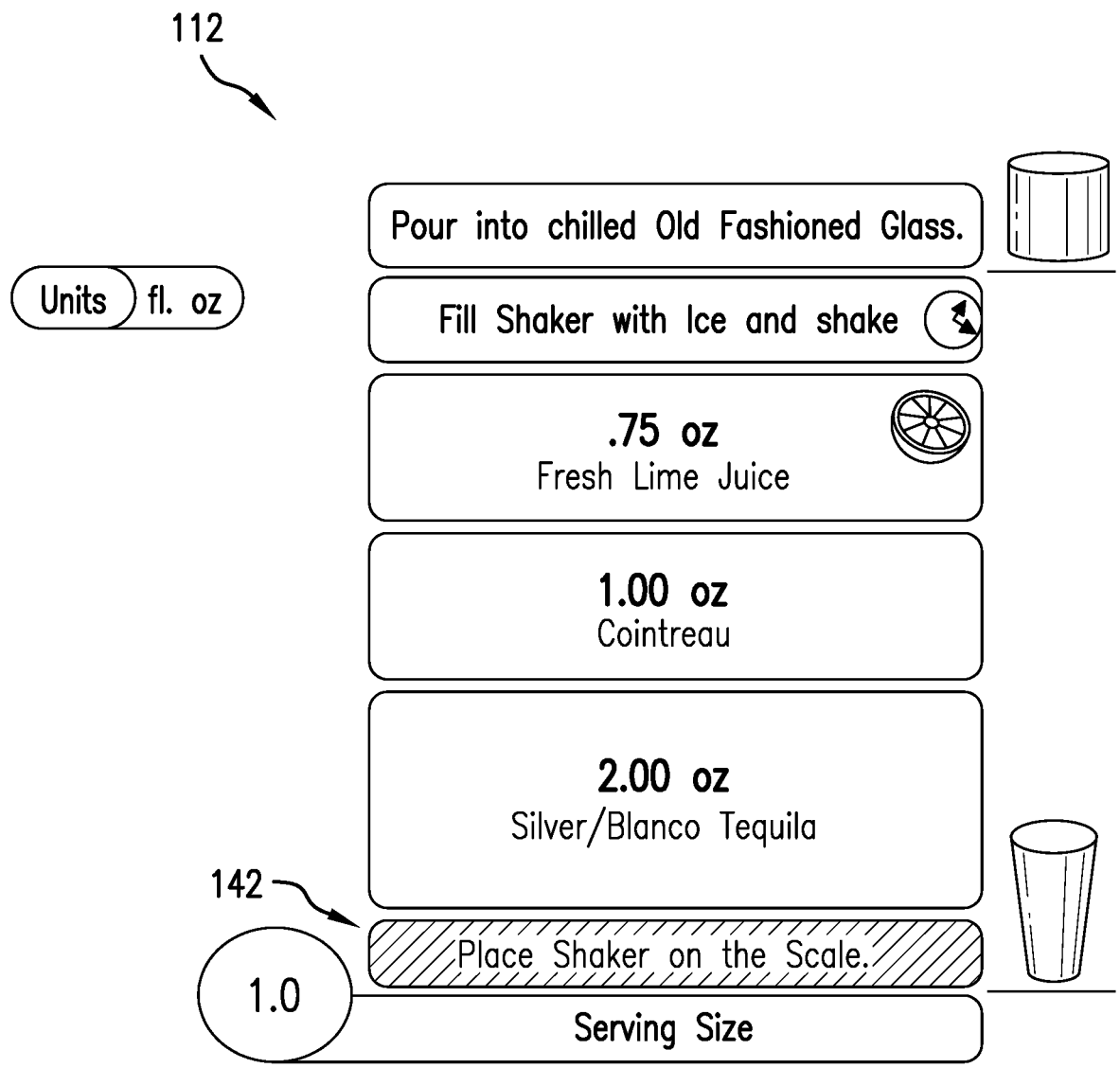
FIG. 10 shows the build column at the beginning of assembling a culinary combination.

FIG. 10 shows the beginning of assembling a culinary combination. A first recipe block 142 is active. The active status of a recipe block 119 may be shown with the recipe block 119 highlighted, enlarged, or in some other enhanced manner. In this case, the first recipe block 142 is enhanced by highlighting it with a special color. The first recipe block 142 is a recipe action block 120 representing the action of placing the first container on the smart scale 102. Before advancing to the next recipe block, any weight added to the smart scale 102 will be automatically zeroed (commonly called a "tare") before measuring the next ingredient. The target container icon 118 can also be highlighted or animated or otherwise enhanced to indicate that it has been detected (see FIG. 11)

Figure 11:
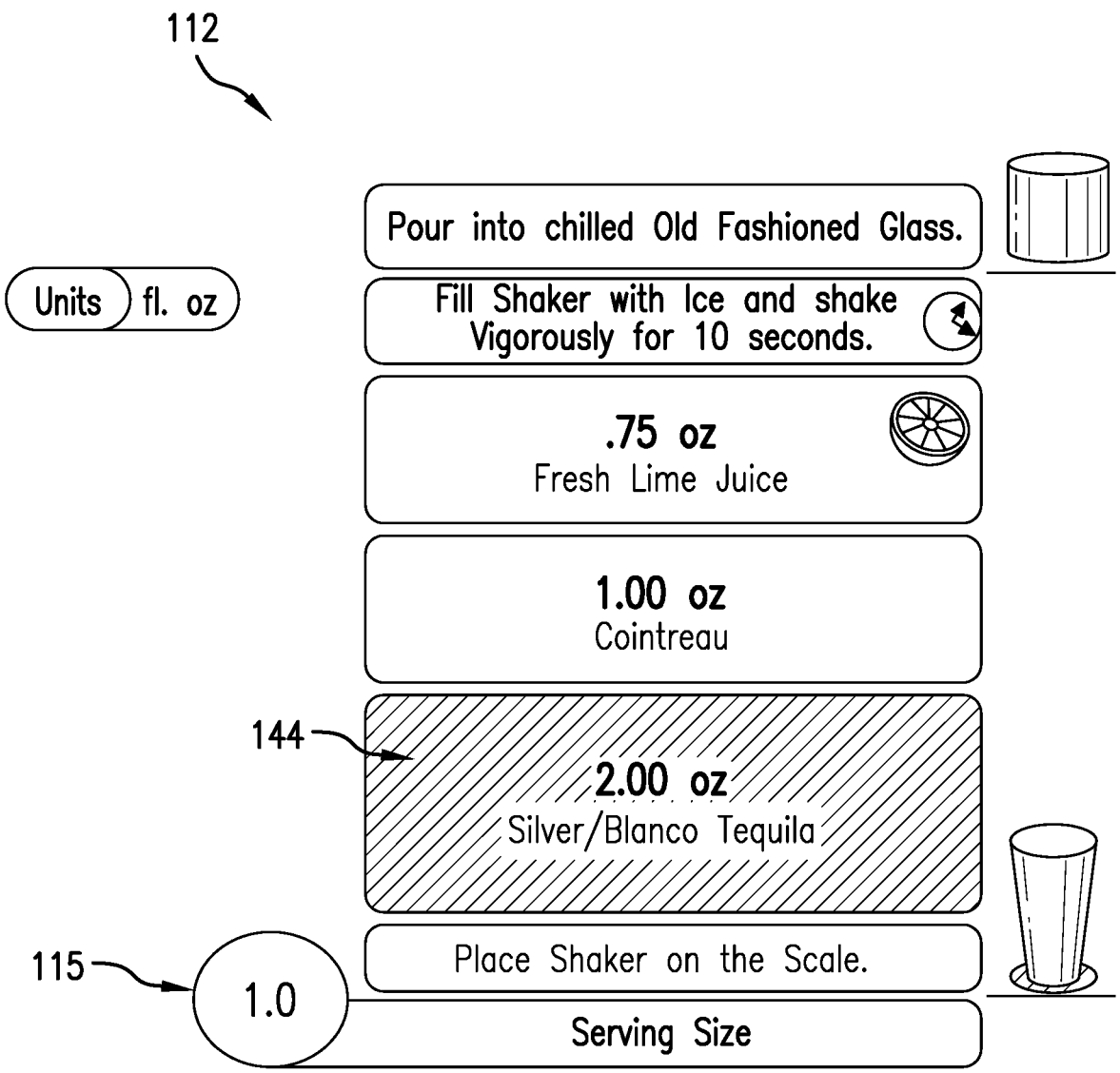
FIG. 11 shows the build column of FIG. 10 in which the recipe has advanced to the next recipe block.

In FIG. 11, the app has advanced the recipe to the next recipe block. There are several options to trigger a recipe advance. These options can be user selectable. Some options include: Weight-based auto-advance; Audio command advance; Recipe Block selection; and Scale button navigation.

Weight-Based Auto-Advance:

This option applies to events that involve a measureable weight change. Some examples of events include:

Placing a target container on the smart scale 102: The culinary ratio system 100 can wait for a measureable weight change followed by a short period of inactivity. It then performs a "tare" and advance to the next recipe block. The user can also adjust the period of inactivity for weight-based auto-advance.

Removing a target container from the smart scale 102: For this action the culinary ratio system 100 would look for weight to be removed from the smart scale 102. An example for this is the 5th recipe block in FIG. 10 where the shaker will need to be removed for mixing/shaking. The automatic timer can start once the shaker is removed from the smart scale 102.

The target amount of an ingredient has been measured: Once the culinary ratio system 100 detects that the target amount has been achieved, followed by a short period of inactivity, it then performs a "tare" and advances to the next recipe block. The user can also adjust the period of inactivity for weight-based auto-advance.

Audio Command Advance:

A microphone may be monitored for vocal commands. The microphone may be mounted in the smart scale 102, built into the smart device 104, or connected to the smart device 104 by some other means such as Bluetooth. Some examples of possible vocal commands are:

"Next": advances to the next recipe block.
"Lime Juice": advances to a specific recipe block.
"Back": moves to the previous recipe block.
"Recalculate" or "Scale": recalculates the overall scale of the recipe using the current measured amount of an ingredient.
"Start Timer": starts a timer.

Recipe Block Selection:

The user can actively choose another recipe block by interacting directly with the smart device 104 using touch screens or pointing devices like mice.

Scale Button Navigation:

Buttons or touch sensors on the smart scale 102 can be used to advance or navigate up and down the build column. These buttons could be labeled "Next" or "Previous" or simply have arrows.

Figure 12:
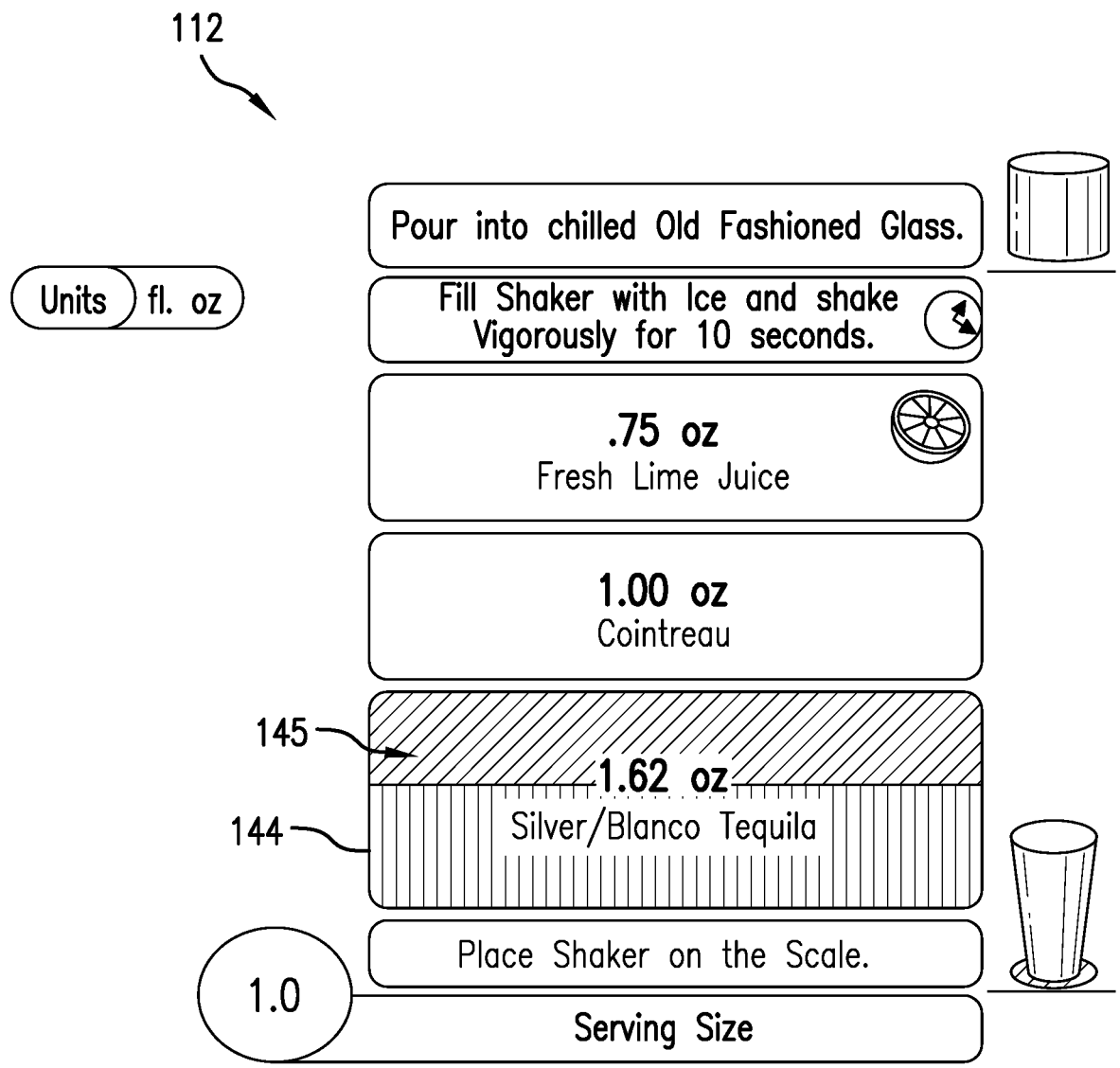
FIG. 12 illustrates how the build column shows progress of an ingredient being added and measured.

FIG. 12 illustrates how the build column 112 shows progress of an ingredient being added and measured. To show progress of the ingredient being added, a portion 145 of the activated recipe block may be displayed in a different manner than a remainder of the activated recipe block, such as a different color. The portion 145 of the activated recipe block displayed differently may be proportional to a ratio of the measured amount of the ingredient being added compared to its target amount. For example, the second recipe block 144 labeled "Silver/Blanco Tequila" in FIG. 12 is the activated recipe block. The second recipe block 144 initially is completed filled with a first color (e.g. green) that indicates that it is the active recipe block. Once a minimum threshold weight increase is detected (this threshold can be set based on the ingredient or amount to be weighed; or adjusted by the user or recipe author), the proportional amount measured is displayed as a portion 145 of the second recipe block 144 in a second color (e.g. yellow) from the bottom of the second recipe block 144. As the measured amount increases, a fill-line between the first and second colored portions of the second recipe block 144 rises. This serves a very clear visual guide for the user. The current measured amount may also be displayed in the block. This numeric value reflects the current measured amount.

Figure 13:
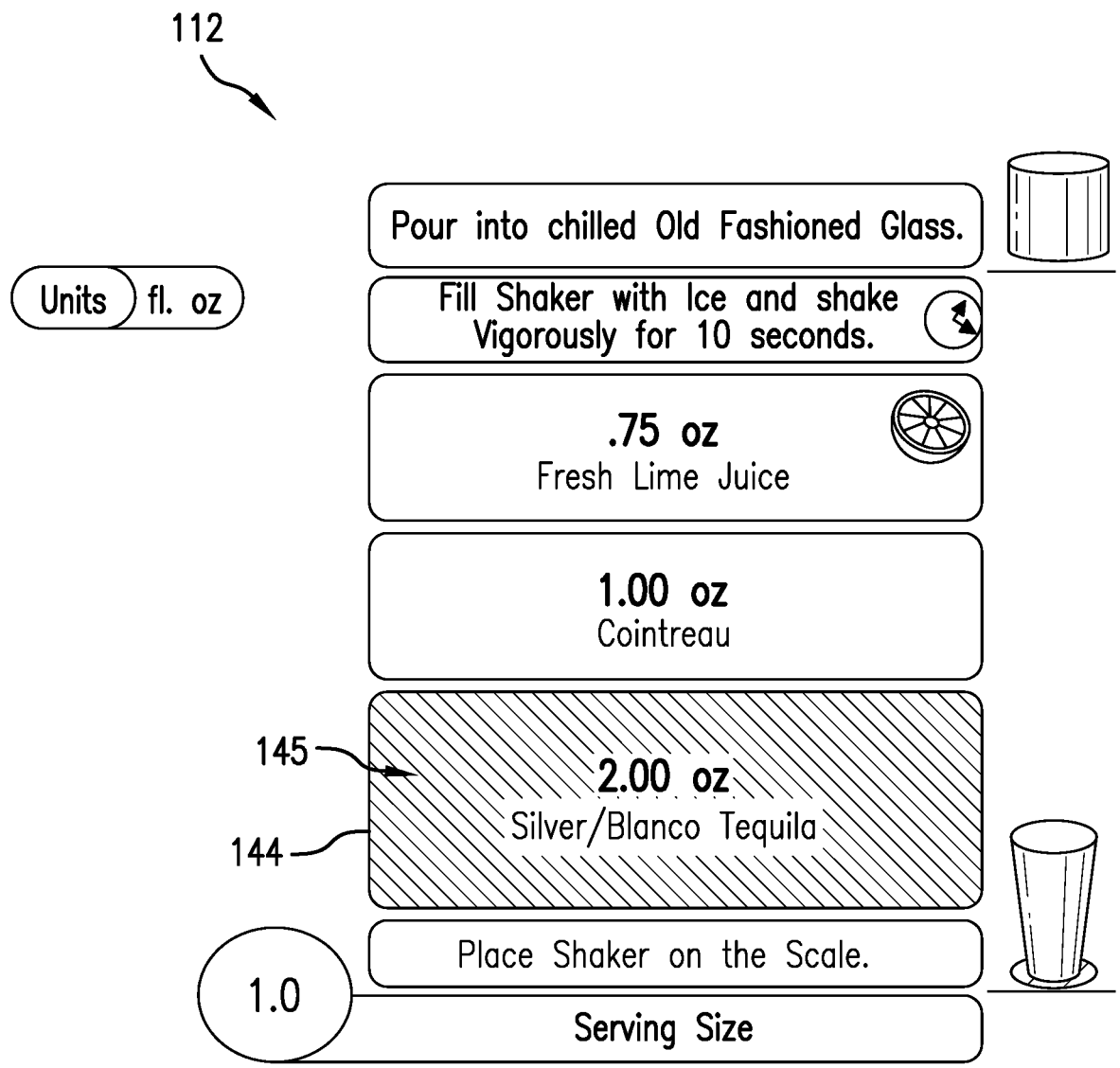
FIG. 13 shows a completed ingredient step.

FIG. 13 shows a completed ingredient step. The second recipe block 144 labeled "Silver/Blanco Tequila" is filled completely. In the example, the fill color is changed to a third color (e.g. red) indicating "stop" to the user. At this point, the system can auto-advance or be advanced directly by the user to another recipe block.

Figure 14:
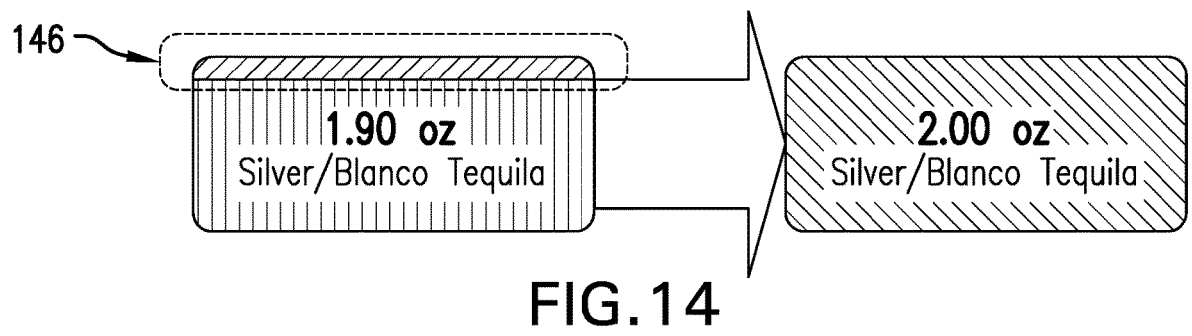
FIG. 14 is a graphical representation of a dead-band that extends below and above the target amount.

When adding ingredients it may be too much to ask any human to add the perfect amount with double-digit accuracy. FIG. 14 is a graphical representation of a dead-band 146 that extends below and above the target amount. The dead-band has an upper threshold and a lower threshold. As the measured amount enters the dead-band, the app indicates to the user to stop pouring. As in FIG. 13, this is done by filling the entire activated recipe block with the third color. This dead-band may be a simple percentage of the target amount. However, the percentage could be framed with pre-defined minimums or maximums to make sure the measurement process is human friendly. The recipe and/or the user may also adjust the dead-band.

Figure 15:
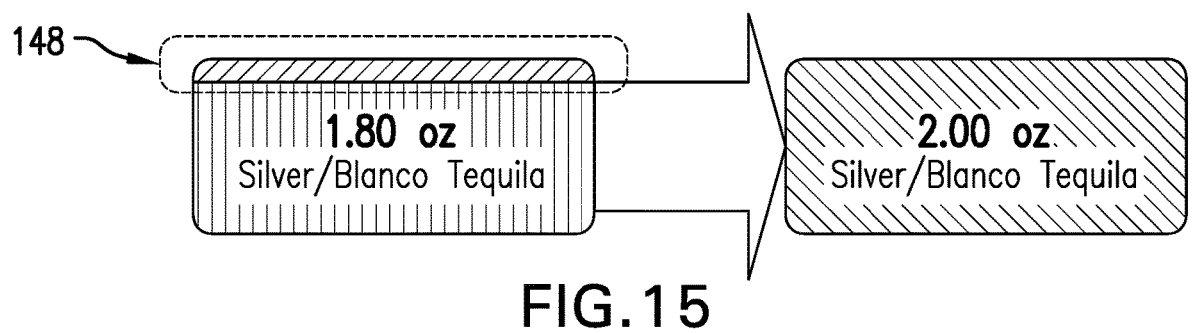
FIG. 15 shows a graphical representation of an off-center dead-band.

For ingredients that are added by pouring it can be helpful if the dead-band is off-center and to make it easier for the user to get close to the target amount. FIG. 15 shows a graphical representation of an off-center dead-band 148 that has a lower threshold that is more distant from the target amount than is the upper threshold. This lower threshold could even be adjusted based on the pour rate.

Figure 16:
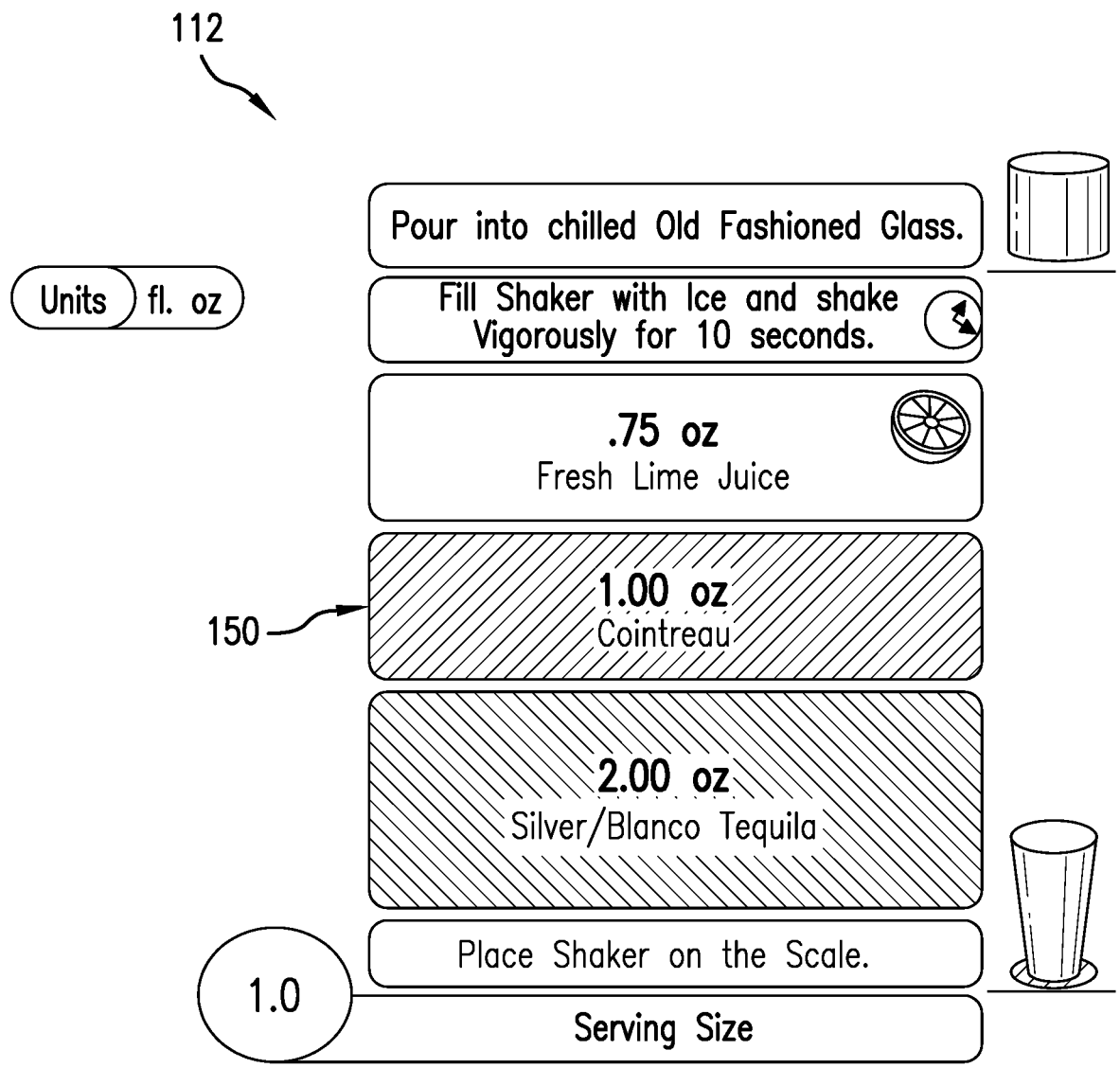
FIG. 16 shows advancement to the next recipe block representing the next step in the recipe.

FIG. 16 shows advancement to the next recipe block 119 representing the next step in the recipe. The second recipe block 144 ("Silver/Blanco Tequila") is shown as completed, as indicated by being completely filled with the third fill color (red, in these examples). A third recipe block 150 ("Cointreau") is the activated recipe block, as indicated by the first fill color (green, in these examples). Possible methods for this advancement are discussed with FIG. 11.

Figure 17:
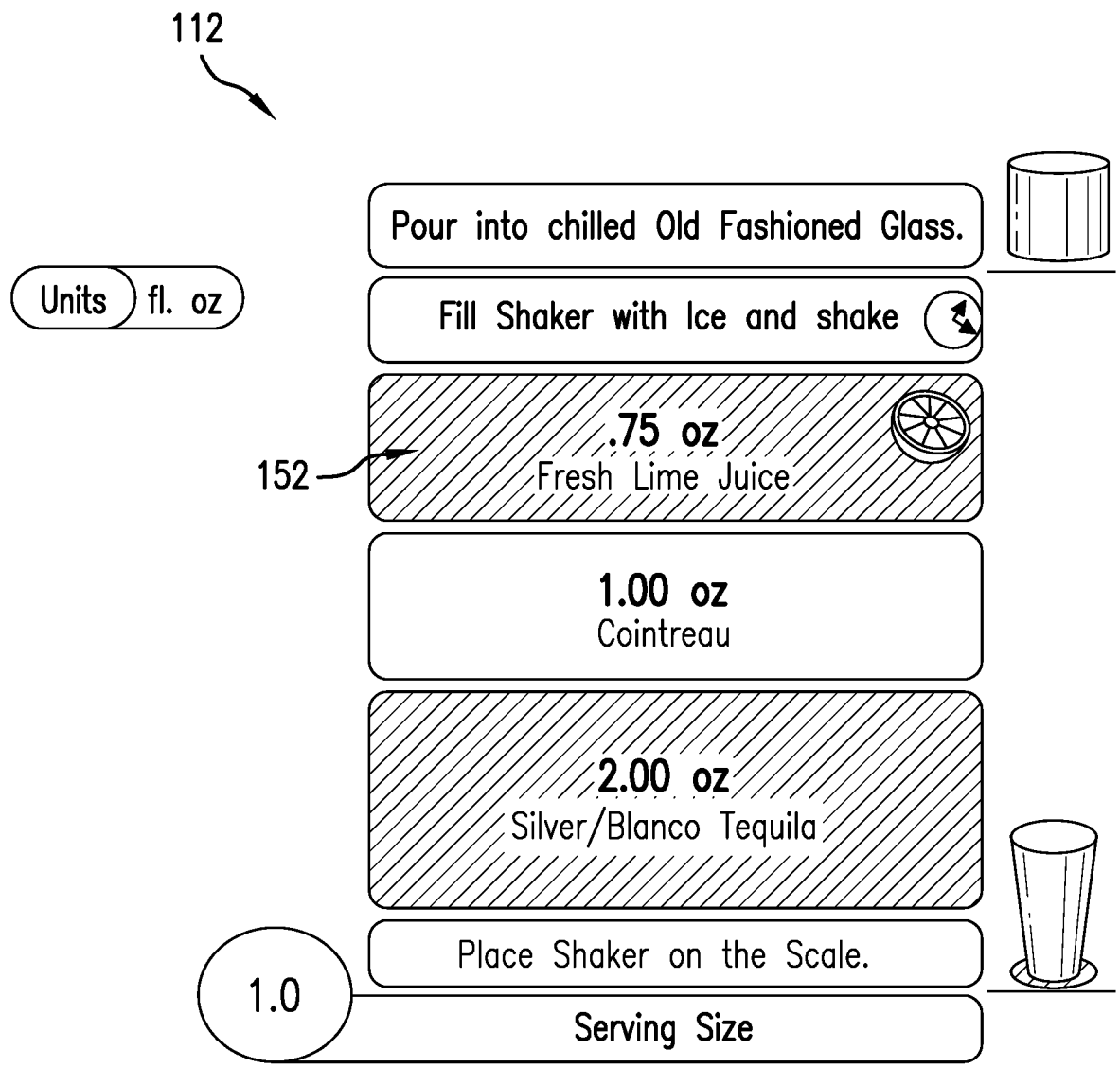
FIG. 17 shows an example of how the user can choose the active ingredient.

The user can choose the active ingredient at any time. FIG. 17 shows an example of this. The user has selected a fourth recipe block 152 ("Lime Juice") as the activated block. Lime Juice will now be added before the Cointreau.

Figure 18:
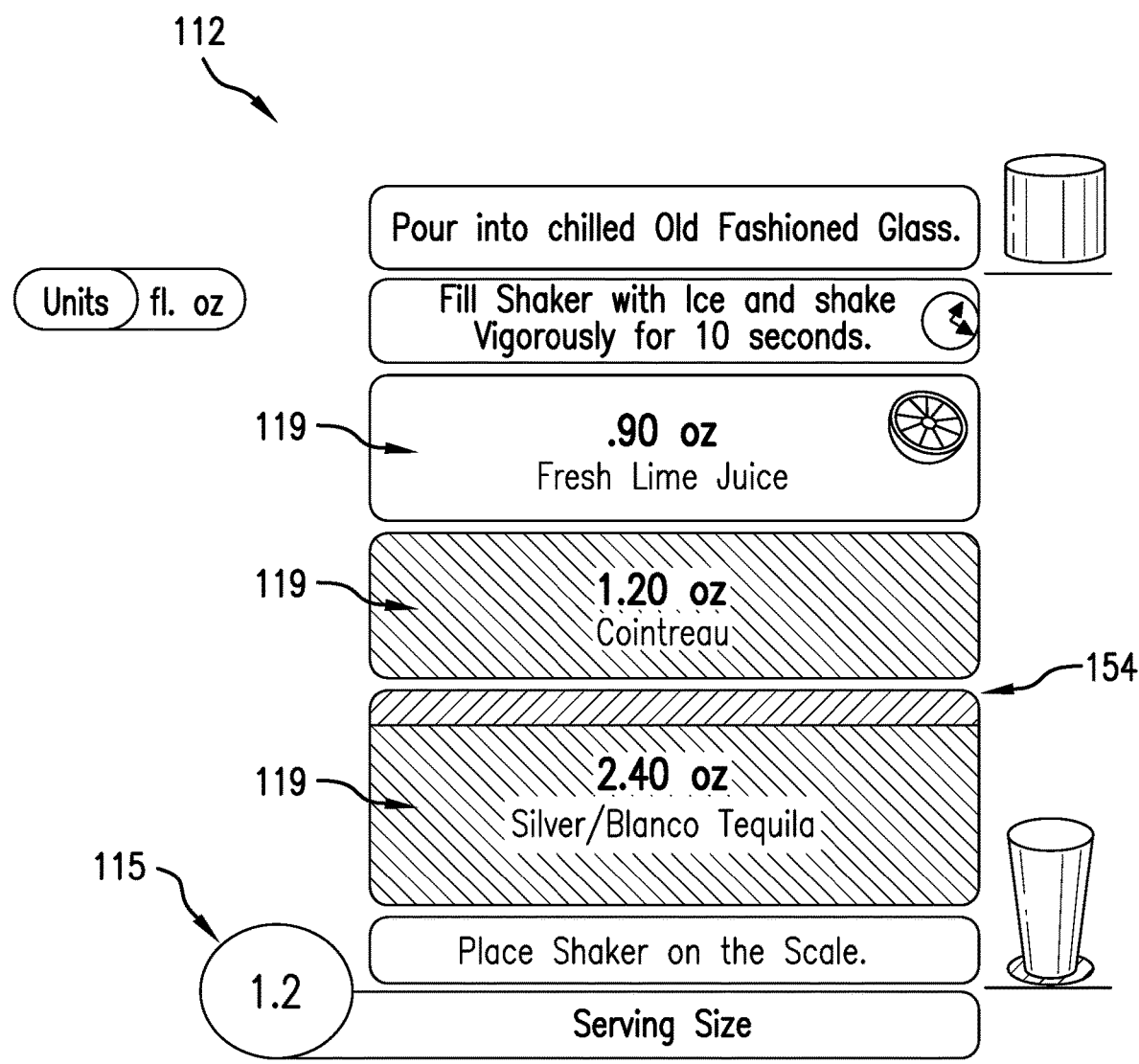
FIG. 18 shows how the culinary ratio is maintained by automatically tracking ingredient amounts that go beyond their dead-bands.

FIG. 18 shows how the culinary ratio is maintained by automatically tracking ingredient amounts that go beyond their dead-bands. When this happens, the entire recipe is adjusted in real-time. As the active ingredient measurement increases above the upper threshold of its dead-band, the recipe scaling factor/serving size and the other ingredient target amounts are adjusted. Any previous complete recipe ingredient block 122 will display an adjustment gap 154 at the top of the recipe ingredient block 122 in a different color than the rest of the recipe ingredient block 122. The adjustment gap 154 represents an adjustment amount for that ingredient that is the difference between the new target amount and the old target amount. The adjustment gap 154 is a portion of the recipe ingredient block 122 that is proportional to the adjustment amount compared to the new target amount. The user can then choose to select previous recipe ingredient blocks 122 and add enough of the associated ingredient to reach the new target amount. In the example of FIG. 18, the user has added 1.20 oz. of Cointreau instead of the target amount of 1.0 oz. The app has adjusted the scaling factor of the recipe from 1.0 to 1.2 to compensate. This changes the target amounts of the other ingredients, including the target amount of the Tequila from 2.0 oz. to 2.4 oz. The second recipe block 144 ("tequila") is now shown with an adjustment gap 154 in the first color (green) that indicates that it is the activated recipe block. The user can then add more of the associated ingredient ("tequila") to top it off to the new target amount of 2.4 oz.

Figure 19:
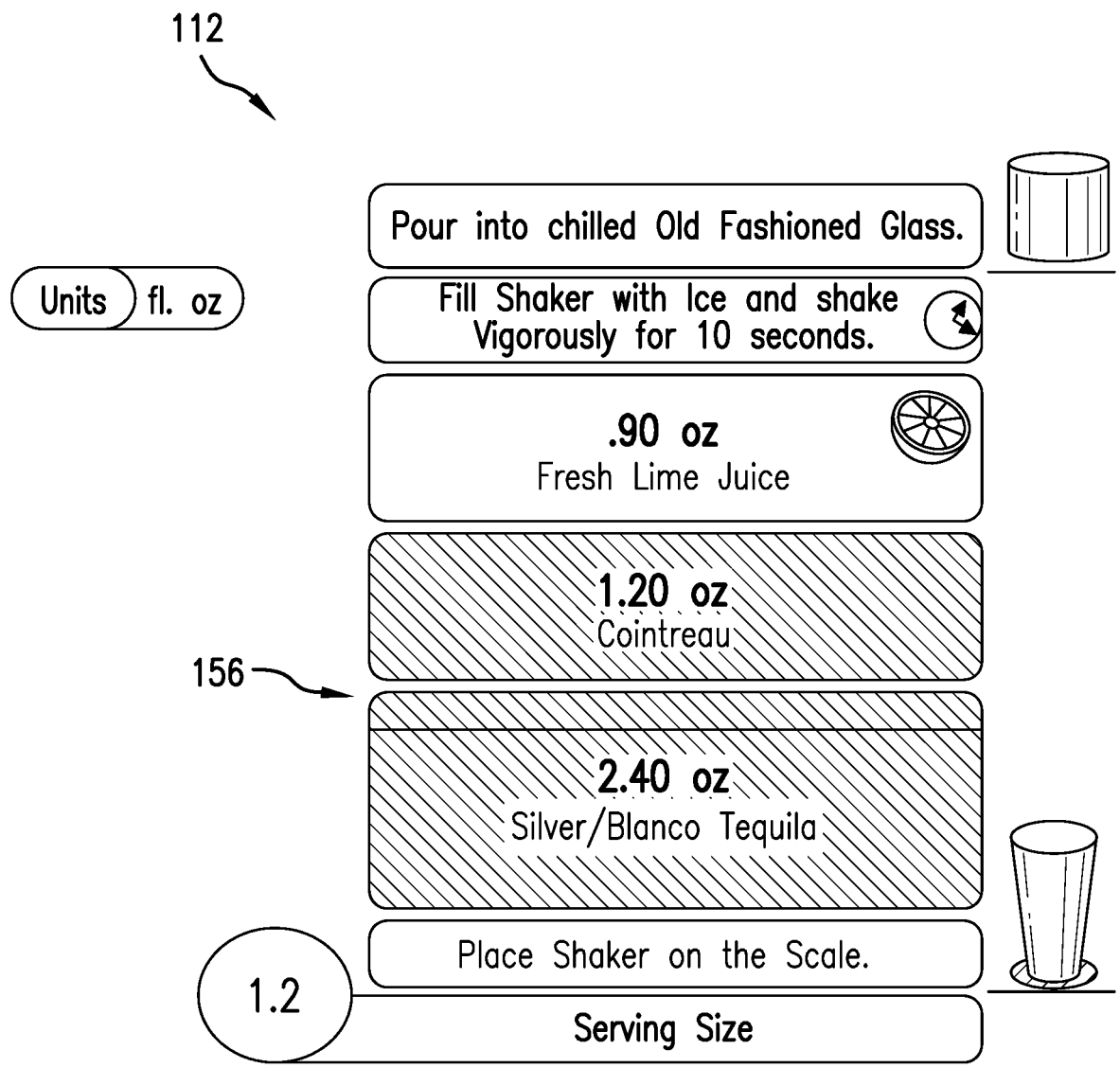
FIG. 19 shows the build column displaying an ingredient event.

The culinary ratio system 100 keeps an ingredient history of ingredient events. An ingredient event is essentially any measured ingredient activity occurring out-of-order or between periods of inactivity. Each significant ingredient event is delineated graphically for the user. FIG. 19 shows such an event for the second recipe block 144 ("tequila"). Continuing the example of FIG. 18, after the target amount of the second recipe block 144 ("tequila") was adjusted to 2.4 oz., the user made a second pour of tequila. This second tequila ingredient event is recorded in the ingredient history and shown as an ingredient event region 156 within the second recipe block 144 separated from the rest of the block by a horizontal line.

Figures 20, 21:
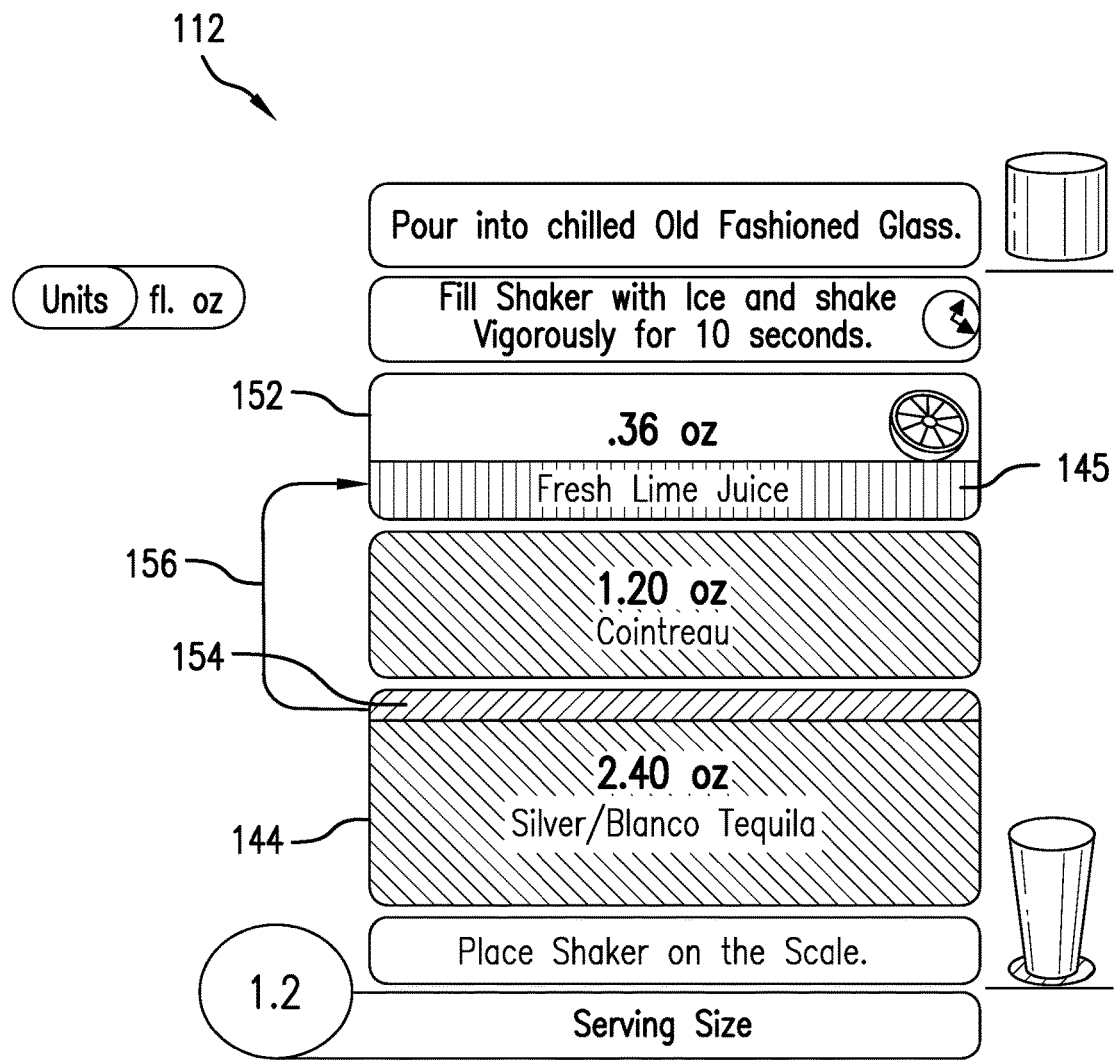
FIG. 20 shows how a user can correct a mistaken ingredient event.
FIG. 21 shows an ingredient history table before edit and the ingredient history table after edit.

The ingredient history is particularly useful for correcting mistakes. If the user accidentally added "lime juice" while the second recipe block 144 ("tequila") is active, this will be recorded as its own ingredient event. The user can correct this mistake by selecting the ingredient event region 156 related to the mistake and moving it to the fourth recipe block 152 ("Lime Juice"). This correction is shown in FIG. 20.

The ingredient history is tracked in an ingredient history table. FIG. 21 shows the ingredient history table before edit 158 and the ingredient history table after edit 160. Each entry has an ingredient and the measured amount for that event. The history starts with the first event and goes down chronologically. The third event lists the lime juice event as tequila. Once the user corrects this by dragging that amount to the fourth recipe block 152 ("Lime Juice"), the table shows the correction. The total amount for any ingredient is the sum of its history.

Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application. As such, the scope of the invention should not be limited by the particular embodiments herein described but should be defined only by the appended claims and equivalents thereof.

What is claimed is:

1. A method for a smart device with an integral graphical display to assist a user in assembling a culinary combination according to a recipe, the recipe identifying one or more ingredients and one or more target amounts, each of the ingredients associated with one of the target amounts, the method comprising:

receiving weight data from a digital kitchen scale;

determining a tared weight based on the weight data, wherein the tared weight represents weight added to the scale since taring;

displaying one or more recipe blocks, including a first recipe block;

selecting the first recipe block as an active block and a first ingredient associated with the first recipe block as an active ingredient, wherein the first ingredient is one of the one or more ingredients, then selecting a target amount for the first ingredient as the target amount for the active ingredient, and then taring the tared weight;

displaying the active block in an enhanced manner;

determining a measured amount of the active ingredient based on the tared weight;

displaying a progress of the measured amount of the active ingredient; and causing the graphical display to display the progress of the measured amount of the active ingredient by displaying a fill-line within the active block, the fill-line rising as the measured amount of the active ingredient increases.

2. A method for a smart device with an integral graphical display to assist a user in assembling a culinary combination according to a recipe, the recipe identifying one or more ingredients and one or more target amounts, each of the ingredients associated with one of the target amounts, the method comprising:

receiving weight data from a digital kitchen scale;

determining a tared weight based on the weight data, wherein the tared weight represents weight added to the scale since taring;

displaying one or more recipe blocks, including a first recipe block;

selecting the first recipe block as an active block and a first ingredient associated with the first recipe block as an active ingredient, wherein the first ingredient is one of the one or more ingredients, then selecting a target amount for the first ingredient as the target amount for the active ingredient, and then taring the tared weight;

displaying the active block in an enhanced manner;

determining a measured amount of the active ingredient based on the tared weight;

displaying a progress of the measured amount of the active ingredient; and causing the graphical display to display progress of the measured amount of the active ingredient by displaying a portion of the active block in a different manner than a remainder of the active block, wherein the portion of the active block displayed differently is proportional to a ratio of the measured amount of the active ingredient compared to the target amount for the active ingredient.

3. A method for a smart device with an integral graphical display to assist a user in assembling a culinary combination according to a recipe, the recipe identifying one or more ingredients and one or more target amounts, each of the ingredients associated with one of the target amounts, the method comprising:

receiving weight data from a digital kitchen scale;

determining a tared weight based on the weight data, wherein the tared weight represents weight added to the scale since taring;

displaying one or more recipe blocks, including a first recipe block;

selecting the first recipe block as an active block and a first ingredient associated with the first recipe block as an active ingredient, wherein the first ingredient is one of the one or more ingredients, then selecting a target amount for the first ingredient as the target amount for the active ingredient, and then taring the tared weight;

displaying the active block in an enhanced manner;

determining a measured amount of the active ingredient based on the tared weight;

displaying a progress of the measured amount of the active ingredient; and displaying a first portion of the active block in a different manner than a second portion of the active block, wherein a ratio of the first portion of the active block displayed to the second portion of the active block displayed is proportional to a ratio of the measured amount of the active ingredient compared to the target amount for the active ingredient.

4. A method for a smart device with an integral graphical display to assist a user in assembling a culinary combination according to a recipe, the recipe identifying one or more ingredients and one or more target amounts, each of the ingredients associated with one of the target amounts, the method comprising:

receiving weight data from a digital kitchen scale;

determining a tared weight based on the weight data, wherein the tared weight represents weight added to the scale since taring;

displaying one or more recipe blocks, including a first recipe block;

selecting the first recipe block as an active block and a first ingredient associated with the first recipe block as an active ingredient, wherein the first ingredient is one of the one or more ingredients, then selecting a target amount for the first ingredient as the target amount for the active ingredient, and then taring the tared weight;

displaying the active block in an enhanced manner;

determining a measured amount of the active ingredient based on the tared weight;

displaying a progress of the measured amount of the active ingredient; and adjusting the target amounts for the ingredients of the recipe based on a scaling factor of the recipe; and changing the scaling factor, if the measured amount of the active ingredient exceeds an upper threshold, wherein the upper threshold is greater than the target amount for the active ingredient, wherein the scaling factor is changed such that the target amount of the active ingredient becomes the measured amount of the active ingredient.

5. A method for a smart device with an integral graphical display to assist a user in assembling a culinary combination according to a recipe, the recipe identifying one or more ingredients and one or more target amounts, each of the ingredients associated with one of the target amounts, the method comprising:

expanding the active block in size on the graphical display.

6. A method for a smart device with an integral graphical display to assist a user in assembling a culinary combination according to a recipe, the recipe identifying one or more ingredients and one or more target amounts, each of the ingredients associated with one of the target amounts, the method comprising:

receiving weight data from a digital kitchen scale;

determining a tared weight based on the weight data, wherein the tared weight represents weight added to the scale since taring;

selecting a first ingredient as an active ingredient, wherein the first ingredient is one of the one or more ingredients, then selecting a target amount for the first ingredient as the target amount for the active ingredient, and then taring the tared weight;

determining a measured amount of the active ingredient based on the tared weight;

causing the graphical display to display progress of the measured amount of the active ingredient; and de-selecting the first ingredient as the active ingredient and selecting a second ingredient as the active ingredient if the smart device determines the measured amount of the active ingredient is more than a lower threshold and less than an upper threshold followed by a period of inactivity, wherein the period of inactivity is a predetermined measure of time for the smart device to determine the user has stopped taking an action that changes the tared weight, wherein the second ingredient is one of the one or more ingredients, wherein the lower threshold is lower than the target amount for the active ingredient, wherein the upper threshold is greater than the target amount for the active ingredient.

7. The method of claim 6, wherein the upper threshold is closer to the target amount for the active ingredient than is the lower threshold.

8. A method for a smart device with an integral graphical display to assist a user in assembling a culinary combination according to a recipe, the recipe identifying one or more ingredients and one or more target amounts, each of the ingredients associated with one of the target amounts, the method comprising:

receiving weight data from a digital kitchen scale;

determining a tared weight based on the weight data, wherein the tared weight represents weight added to the scale since taring;

selecting a first ingredient as an active ingredient, wherein the first ingredient is one of the one or more ingredients, then selecting a target amount for the first ingredient as the target amount for the active ingredient, and then taring the tared weight;

determining a measured amount of the active ingredient based on the tared weight;

causing the graphical display to display progress of the measured amount of the active ingredient;

causing the graphical display to display an indication for the user to perform a first action;

performing a second action if the smart device determines the first action has occurred;

wherein the first action comprises removing a container from the scale;

wherein performing the second action comprises starting a timer; and wherein the smart device determines the first action has occurred by determining the tared weight has decreased.

9. A method for a smart device with an integral graphical display to assist a user in assembling a culinary combination according to a recipe, the recipe identifying one or more ingredients and one or more target amounts, each of the ingredients associated with one of the target amounts, the method comprising:

receiving weight data from a digital kitchen scale;

determining a tared weight based on the weight data, wherein the tared weight represents weight added to the scale since taring;

selecting a first ingredient as an active ingredient, wherein the first ingredient is one of the one or more ingredients, then selecting a target amount for the first ingredient as the target amount for the active ingredient, and then taring the tared weight;

determining a measured amount of the active ingredient based on the tared weight;

causing the graphical display to display progress of the measured amount of the active ingredient;

causing the graphical display to display an indication for the user to perform a first action;

performing a second action if the smart device determines the first action has occurred;

wherein the first action comprises placing a container on the scale;

wherein performing the second action comprises starting a timer; and wherein the smart device determines the first action has occurred by determining the tared weight has increased.

10. A method for a smart device with an integral graphical display to assist a user in assembling a culinary combination according to a recipe, the recipe identifying one or more ingredients and one or more target amounts, each of the ingredients associated with one of the target amounts, the method comprising:

receiving weight data from a digital kitchen scale;

determining a tared weight based on the weight data, wherein the tared weight represents weight added to the scale since taring;

selecting a first ingredient as an active ingredient, wherein the first ingredient is one of the one or more ingredients, then selecting a target amount for the first ingredient as the target amount for the active ingredient, and then taring the tared weight;

determining a measured amount of the active ingredient based on the tared weight;

causing the graphical display to display progress of the measured amount of the active ingredient;

in response to receiving a command from the user, de-selecting the first ingredient as the active ingredient and selecting a second ingredient from the one or more ingredients as the active ingredient;

wherein the one or more recipe ingredients are in a recommended order; and wherein the second ingredient is selected out of the recommend order.

11. A method for a smart device with an integral graphical display to assist a user in assembling a culinary combination according to a recipe, the recipe identifying one or more ingredients and one or more target amounts, each of the ingredients associated with one of the target amounts, the method comprising:

receiving weight data from a digital kitchen scale;

determining a tared weight based on the weight data, wherein the tared weight represents weight added to the scale since taring;

selecting a first ingredient as an active ingredient, wherein the first ingredient is one of the one or more ingredients, then selecting a target amount for the first ingredient as the target amount for the active ingredient, and then taring the tared weight;

determining a measured amount of the active ingredient based on the tared weight;

causing the graphical display to display progress of the measured amount of the active ingredient; and in response to receiving a command from the scale, the smart device de-selecting the first ingredient as the active ingredient and selecting a second ingredient from the one or more ingredients as the active ingredient.

12. A method for a smart device with an integral graphical display to assist a user in assembling a culinary combination according to a recipe, the recipe identifying one or more ingredients and one or more target amounts, each of the ingredients associated with one of the target amounts, the method comprising:

receiving weight data from a digital kitchen scale;

determining a tared weight based on the weight data, wherein the tared weight represents weight added to the scale since taring;

selecting a first ingredient as an active ingredient, wherein the first ingredient is one of the one or more ingredients, then selecting a target amount for the first ingredient as the target amount for the active ingredient, and then taring the tared weight;

determining a measured amount of the active ingredient based on the tared weight;

causing the graphical display to display progress of the measured amount of the active ingredient;

after a first period of inactivity, recording a first ingredient event amount and associating the first ingredient event amount with the active ingredient, wherein the first ingredient event amount is the tared weight at a time the first ingredient event amount was recorded;

after a second period of inactivity, recording a second ingredient event amount and associating the second ingredient event amount with the active ingredient wherein the second ingredient event amount is the tared weight at a time the second ingredient event amount was recorded minus the first ingredient event amount;

wherein the first and second periods of inactivity are each a predetermined measure of time for the smart device to determine the user has stopped taking an action that changes the tared weight; and wherein determining the measured amount of the active ingredient based on the tared weight further comprises determining the measured amount of the active ingredient as a sum of the first ingredient event amount and the second ingredient event amount.

13. The method of claim 12, further comprising:

transferring association, upon user command, of the second ingredient event amount from the active ingredient to a second ingredient, wherein the second ingredient is one of the one or more ingredients of the recipe.

14. A system for assisting a user in assembling a culinary combination, the system comprising:

a digital kitchen scale wirelessly connectable to smart devices;

a smart device wirelessly connectable to the digital kitchen scale, the smart device with a processor, a memory and a graphical display, the smart device having instructions stored in the memory which when executed by the processor, causes the processor to perform steps of a method for assisting the user in assembly the culinary combination according to a recipe, the recipe reciting one or more recipe ingredients, the steps comprising:

causing the graphical display to display a status of the digital kitchen scale when a container is placed on the scale;

causing the graphical display to display a target amount of a first recipe ingredient to be added to the container, the first recipe ingredient one of the one or more recipe ingredients;

causing the graphical display to display a graphical representation of proportional completion status of an addition of the first recipe ingredient synchronized to the addition of the first recipe ingredient into the container; and wherein a second recipe ingredient is presented on the graphical display after the target amount of the first recipe ingredient is reached, the second recipe ingredient one of the one or more recipe ingredients.

15. A system for assisting a user in assembling a culinary combination, the system comprising:

a digital kitchen scale wirelessly connectable to smart devices;

a smart device wirelessly connectable to the digital kitchen scale, the smart device with a processor, a memory and a graphical display, the smart device having instructions stored in the memory which when executed by the processor, causes the processor to perform steps of a method for assisting the user in assembly the culinary combination according to a recipe, the recipe reciting one or more recipe ingredients, the steps comprising:

causing the graphical display to display a status of the digital kitchen scale when a container is placed on the scale;

causing the graphical display to display a target amount of a first recipe ingredient to be added to the container, the first recipe ingredient one of the one or more recipe ingredients;

causing the graphical display to display a graphical representation of proportional completion status of an addition of the first recipe ingredient synchronized to the addition of the first recipe ingredient into the container; and a recipe block comprising a discrete graphical user interface element, smaller in size than a useable area of the graphical display, associated with one of adding an ingredient and action step.

* * * * *